(12) United States Patent
Strayer

(10) Patent No.: US 6,797,728 B2
(45) Date of Patent: Sep. 28, 2004

(54) USE OF INTRACELLULAR CALCIUM CHELATORS TO INCREASE SURFACTANT SECRETION IN THE LUNGS

(75) Inventor: David S. Strayer, Newtown Square, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 10/045,904

(22) Filed: Nov. 7, 2001

(65) Prior Publication Data

US 2002/0148463 A1 Oct. 17, 2002

Related U.S. Application Data

(60) Provisional application No. 60/246,616, filed on Nov. 8, 2000.

(51) Int. Cl.$^7$ .............................................. A61K 31/24

(52) U.S. Cl. ................................. 514/534; 424/DIG. 6; 514/532; 514/567; 514/570; 514/576; 514/646; 514/716; 514/718; 514/721

(58) Field of Search .................... 424/DIG. 6; 514/532, 514/534, 567, 570, 576, 646, 716, 718, 721

(56) References Cited

PUBLICATIONS

STN/CAS online, file EMBASE, Acc. No. 91085875, Doc. No. 1991085875 (Corbet et al., American Journal of the Medical Sciences, vol. 301, No. 2, pp. 102–114 (1991)), Abstract.*
STN/CAS online, file CAPLUS, Acc. No. 1999:341901, Doc. No. 131:115219 (Okumura et al., American Journal of Physiology, vol. 276, No. 5, Pt. 1, pp. L763–L768 (1999)), Abstract.*
STN/CAS online, file JICST–EPlus, Acc. No. 980037481 (Isohama et al., Nippon Yakurigaku Zasshi (Folia Pharmacologica Japonica), vol. 100, pp 120P–125P (1997)), Abstract.*
STN/CAS online, file BIOSIS, Acc. No. 2000:262973, Doc. No. PREV200000262973 (Benito et al., Molecular and Cellular Biochemistry, vol. 205, No. 1–2, pp. 39–44 (Feb. 2000)), Abstract.*
Strayer et al., "Cellular activation by Ca2+ releases from stores in the endoplasmic reticulum but not by increased free Ca2+ in the cytosol", Biochem. J. , vol. 344, pp. 39–46 (1999).*
Aballay, A. Sarrouf, M., Colombo, M., Stahl, P., & L. Mayorga "Zn$^{2+}$ Depletion Blocks Endosome Fusion." Biochem J 312: 919–923, 1995.
Avery, M. & J. Mead "Surface Properties in Relation to Atelectasis and Hyaline Membrane Disease." AM J Dis Child 97: 517–523, 1959.

Benito, E. & M. Bosch "the Inflammatory Cytokines Tumor Necrosis Factor α and Interleukin–1β Stimulate Phosphatidylcholine Secretion in Primary Cultures of Rat Type II Pneumocytes." Mol Cell Biochem 189: 169–176, 1998.
Berridge, M. "Inositol Trisphosphate and Calcium Signalling." Nature 361: 315–325, 1993.
Bian, X., Hughes, F., Huang, Y., Cidlowski, J., & J. Putney "Roles of Cytoplasmic CA$^{2+}$ and Intralcellular CA$^{2+}$ Stores in Induction & Suppression of Apoptosis in S49 Cells." Am J Physiol 272: 1241–1249, 1997.
Blatter, L., & W. Wier "Intracellular Diffusion, Binding, and Compartmentalization of the Fluorescent Calcium Indictors Indo–1 and Fura–2." Biophys J 58: 1491–1499, 1990.
Chander, A., & A. Fisher "Regulation of Lung Surfactant Secretion." Am J Physiol 258: L241–253, 1990.
Dobbs, L., Wright, J., Hawgood, S., Gonzalez, Venstrom, K., & J. Nellenbogen "Pulmonary Surfactant & Its Components Inhibit Secretion of Phosphatidylcholine from Cultured Rat Alveolar Type II Cells." Proc Natl Acad Sci 84: 1010–1014, 1987.
Dorn, C., Rice, W., & F. Singleton "Calcium Mobilization and Response Recovery Following P$_2$–purinoceptor Stimulation of Rat Isolated Alveolar Type II Cells." Br J Pharmacol 97: 163–170, 1989.
Hawgood, S., & K. Shiffer "Stuctures & Properties of the Surfactant–associated Proteins." Annu Rev Physiol 53: 375–394, 1991.
Kuroki, Y., Mason, R., & D. Voelker "Chemical Modifications of Surfactant Protein A Alters High Affinity Binding to Rat Alveolar Type II Cells & Regulation of Phospholipid Secretion*." J Biol Chem 263 (33) 25: 17596–17602, 1988.
Kuroki, Y., Mason, R., & D. Voelker "Alveolar Type II Cells Express a High–affinity Receptor for Pulmonary Surfactant Protein A." Proc Natl Acad Sci USA 85: 5566–5570, 1988.
He, H, Lam, M, Mccormick, T., & C. Distelhorst "Maintenance of Calcium Homeostasis in the Endoplasmic Reticulum by BCL–2." J Cell Biol 138: 1219–1228, 1997.
Ko, W., Wilson, S., & P. Wong "Purine & Pyrimidine Nucleotide Receptors in the Apical Membranes of Equine Cultured Epithelia." Br J Pharmacol 121: 150–156, 1997.
Lewis, J., & A. Jobe "Surfactant & the Adult Respiratory Distress Syndrome." Am Rev Respir Dis 147: 218–233, 1993.

(List continued on next page.)

Primary Examiner—Thurman K. Page
Assistant Examiner—Frank Choi
(74) Attorney, Agent, or Firm—Drinker Biddle & Reath LLP

(57) ABSTRACT

Pulmonary surfactant is required in order to reduce surface tension in the lungs so that less effort is needed to reinflate the lungs after exhalation. A number of diseases and conditions exist that disrupt the normal flow of surfactant secretion, resulting in respiratory distress or failure. The present invention provides a method of treating a patient in respiratory distress syndrome wherein a surfactant deficiency has occurred, thereby restoring a normal respiratory function.

6 Claims, 12 Drawing Sheets

OTHER PUBLICATIONS

Lillie, T., & B. Gomperts "Nucleotides & Divalent Cations As Effectors & Modulators of Exocytosis in Permeabilized Rat Mast Cells." Phil Trans Royal Soc Lond Ser B 336: 25–34, 1992.

Lille, T., & B. Gomperts "Guanine Nucleotide is Essential and $Ca^{2+}$ is a Modulator in the Exocytotic Reaction of Permeabilized Rat Mast Cells." Biochem J 288: 181–187, 1992.

Mikoshiba, K. "the $InsP_3$ Receptor & Intracellular $Ca^{2+}$ Signalling." Curr Opin Neurobiol 7: 339–345, 1997.

Miyata, H., Silverman, H., Sollott, S., Lakatta, E., Stern, M., & R. Hansford "Measurement of Mitochondria Free $Ca^{2+}$ Concentration in Living Single Rat Cardiac Myocytes." Am J Physiol 261: H1123–H1134, 1991.

Nogee, L., Garnier, G., Dietz, H., Singer, L., Murphy, A., & D. deMello "A Mutation in the Surfactant Protein B Gene Responsible for Fatal Neonatal Respiratory disease in Multiple Kindreds." J Clin Invest 93: 1860–1863, 1994.

Pian, M., Dobbs, L., & N. Düzgünes "Positive Correlation Between Cytosolic Free Calcium & Surfactant Secretion in Cultured Rat Alveolar Type II Cells." Biochim Biophys Acta 960: 43–53, 1988.

Putney, J., & G. Bird "The Signal for Capacitative Calcium Entry." Cell 75: 199–201, 1993.

Renard–Rooney, D., Hajnóczky, G., Seitz, m., Schneider, T., & A. Thomas "Imaging of Inositol 1,4,5–Trisphosphate–induced $CA^{2+}$ Fluxes in Single Permeabilized Hepatocytes." J Biol Chem 268 (31) 5: 23601–23610, 1993.

Rice, W., Ross, G., Singleton, F., Dingle, S., & J. Whitsett "Surfactant–associated Protein Inhibits Phospholipid Secretion From Type II Cells." J Appl Physiol 63: 692–698, 1987.

Richardson, A., & C. Taylor "Effects of $Ca^{2+}$ Chelators on Purified Inositol 1,4,5–Trisphosphate (InsP$_3$) Receptors & InsP$_3$–stimulated $Ca^{2+}$ Mobilization*." J Biol Chem 268 (16) 5: 11528–11533, 1993.

Rooney, S., Young, S., & S. Mendelson "Molecular & Cellular Processing of Lung Surfactant." FASEB J 8: 957–967, 1994.

Rotondo, S., Evangelista, V., Manarini, S., deGaetano, G., & C. Cerletti "Different Requirement of Intracellular Calcium & Protein Kinase C for Arachidonic Acid Release & Serotonin Secretion in Cathepsin G–activated Platelets." Thromb Haemost 78: 919–925, 1997.

Sano, K., Voelker, D., & R. Mason "Effect of Secretagogues on Cytoplasmic Free Calcium in Alveolar Type II Epithelial Cells." Am J Physiol 253: C679–C686, 1987.

Sen, N., & A. Chander "Alkalosis– & ATP–induced Increases in the Diacylglycerol Pool in Alveolar Type II Cells are Derived from Phosphatidylcholine and Phosphatidylinositol." Biochem J 298: 681–687, 1994.

Strayer, D., Pinder, R., & A. Chandler "Receptor–mediated Regulation of Pulmon ary Surfactant Secretion." Exp Cell Res 226: 90–97, 1996.

Strayer, D., Korutla, L. & A. Thomas "Surfactant Protein–A Receptor –Mediated Inhibition of Calcium Signaling in Alveolar Type II Cells." Rec Signal Transduc 7 (2), 111–120, 1997.

Suchard, S., & L. Boxer Exocytosis of a Subpopulation of Sepcific Granules Coincides with $H_2O_2$ Production in Adherent Human Neutrophils[1]. J Immunol 152: 290–300, 1994.

Sugden, P., & A. Clerk "Regulation of the ERK Subgroup of MAP Kinase Cascades Through G Protein–coupled Receptors." Cell Signal 9 (5): 337–351, 1997.

Thastrup, O., Cullen, P., Drøbak, B., Hanley, M., & A. Dawson "Thapsigargin, a Tumor Promoter, Discharges Intracellular $Ca^{2+}$ Stores by Specific Inhibition of the Endoplasmic Reticulum $Ca^{2+}$ –ATPase." Proc Natl Acad Sci USA 87: 2466–2470, 1990.

Vainio, M., Saijonmaa, O., Fyhrquist, F., & K. Törnquist "Purinergic Agonists Stimulate the Secretion of Endothelin–1 in Rat Thyroid FRTL–5 Cells." J Cell Physiol 169: 538–543, 1996.

Xu, J., Liu, M., Liu, J., Caniggia, I., & M. Post "Mechanical Strain Induces Constitutive & Regulated Secretion of Glycosaminoglycans & Proteoglycans in Fetal Lung Cells." J Cell Sci 109: 1605–1613, 1996.

Kuroki, Y., Shiratori, M., Murata, Y., & Y. Akino "Surfactant Protein D (SP–D) Counteracts the Inhibitory Effect of Surfactant Protein A (SP–A) on Phospholipid Secretion by Alveolar Type II Cells." Biochem J 279: 115–119, 1991.

* cited by examiner

Change in [Ca$^{2+}$], in response to BAPTA-AM

USE OF INTRACELLULAR CALCIUM CHELATORS TO INCREASE SURFACTANT SECRETION IN THE LUNGS

CROSS REFERENCE TO RELATED APPLICATIONS

This application claims priority under 35 U.S.C. §119 based upon U.S. Provisional Application No: 60/246,616 filed Nov. 8, 2000.

GOVERNMENT RIGHTS IN THE INVENTION

This invention was made with government support under grants GM55436, and AA07186 awarded by USPHS. The government has certain rights in the invention.

FIELD OF THE INVENTION

The present invention relates to the fields of cellular biology and internal medicine and to a method of treating or preventing a respiratory distress syndrome and, more particularly, to the activation and regulation of surfactant secretion in type II alveolar pneumocytes.

BACKGROUND OF THE INVENTION

A physiologically active substance, called "pulmonary surfactant" exists in the animal lungs. Pulmonary surfactant is mainly biosynthesized in and secreted from type II epithelial cells of the alveoli and is known to be present as an internal lining of the wall of t he whole respiratory tract including the alveolar region. It is known that pulmonary surfactant reduces the surface tension of the alveoli and prevents collapse of the alveoli. The ability of surfactant to reduce surface tension means that less effort is needed to re-inflate the lungs after the alveoli are drained of air during exhalation. The less effort required, the less trauma to the lung itself in the course of normal breathing.

In addition, pulmonary surfactant plays an important role as a defense mechanism in the entire respiratory tract. It is well documented that it prevents pulmonary edema and has preventative effects on bacterial infection, viral infection, as well as on atmospheric pollutants and antigens which induce inflammation of the respiratory tract or asthmatic attacks. Pulmonary surfactant is also known to play an important role in lubricating the respiratory lumen and expelling foreign matter from the respiratory tract by activating mucociliary transport.

Pulmonary surfactant is a complex mixture of proteins and phospholipids. There are four known proteins in alveolar surfactant; SP-A, -B, -C, and -D. SP-B and -C are small, very hydrophobic proteins that interact with phospholipids to lower alveolar surface tension. SP-D is a 43 kDa apo-protein of uncertain function. Like SP-A, SP-D has collagen-like domains. SP-A is a moderately hydrophobic 29–36 kDa apo-protein. It reportedly stabilizes the phospholipid structure and promotes interactions between phospholipids. It also appears to be important in regulating surfactant secretion. These proteins, together with phospholipids, are secreted from alveolar type II pneumocytes and form the air-liquid interphase in the alveoli and comprise what is referred to herein as "alveolar surfactant".

Because of its various physiological functions in the respiratory system, qualitative and quantitative changes of pulmonary surfactant seem to be related to the onset of or aggravation of many conditions. Accordingly, the modulation of secretion of pulmonary surfactant will allow for the treatment or prevention of various respiratory conditions, including, but not limited to, acute respiratory failure such as infant or adult respiratory distress syndrome, bronchitis, infectious disease and chronic respiratory failure.

The mechanism(s) that activate and regulate surfactant secretion are not well understood, but evidence suggests that calcium is important in signaling this process. The role of calcium signaling in the activation of surfactant secretion reflects changes in the concentration of free calcium in cytosol stores (lumenal calcium concentration, or $[Ca^{2+}]_l$) and is independent of the cytosolic calcium concentration ($[Ca^{2+}]_i$).

Surfactant secretion by type II cells is often studied in vitro, using receptor-binding secretagogues such as purines or α-adrenergic agonists. (Sano, et al, *Am. J. Physiol.* 253: C679–C686, 1987; Sen, et al, *Biochem. J.* 298:681–687, 1994; Strayer, et al, *Exp. Cell Res.* 226: 90–97, 1996; Strayer, et al, *Rec. Signal Transd.* 7: 111–120, 1997). Surfactant secretion may also be activated independently of cell membrane receptors. Calcium ionophores (such as ionomycin (Io), are surfactant secretagogues that lack plasma membrane receptors. They release calcium from ER stores directly, and carry calcium from outside the cell into the cytosol. The secretagogue activity for thapsigargin (TG) also stimulates surfactant secretion. (Strayer, et al, *Rec. Signal Transd.* 7: 111–120, 1997; Thastrop, et al, *Proc. Natl. Acad. Sci. USA* 87: 2466–2470, 1990). Thapsigargin directly inhibits the $Ca^{2+}$-dependent ATPase pump that maintains the calcium gradient at the ER stores, thereby acting directly on stores to increase $[Ca^{2+}]_i$. These secretagogues emphasize the importance of ER calcium stores in signaling surfactant secretion (Strayer, et al, *Exp. Cell Res.* 226: 90–97, 1996). With or without receptor mediation, these secretagogues elicit rapid, large changes in $[Ca^{2+}]_i$. Calcium is released from intracellular stores, followed by influx of calcium through plasma membrane calcium channels. (Strayer, et al, *Rec. Signal Transd.* 7: 111–120, 1997; Berridge, M J, *Nature*, 361: 315–325, 1993). A potent surfactant secretagogue that is an exception are the phorbal esters. They stimulate surfactant secretion without altering $[Ca^{2+}]_i$. (Sano, et al, *Am. J. Physiol.* 253: C679–C686, 1987).

One of the surfactant proteins, SP-A, decreases secretagogue-stimulated surfactant secretion. (Strayer, et al, *Exp. Cell Res* 222: 681–687, 1994; Dobbs, et al, *Proc. Natl. Acad. Sci. USA* 84:1010–1014, 1987; Hawgood and Shiffer, *Annu. Rev. Physiol.* 53: 375–394, 1991; Rice, et al, *J. Appl. Physiol.* 63: 692–698, 1987 Rooney, et al, *FASEB J.* 8, 957–967, 1994). SP-A binds a type II cell membrane receptor (SPAR) to prevent the $Ca^{2+}$ release elicited by all the above secretagogues, including those acting directly on stores (Io and TG). (Strayer, et al, *Rec. Signal Transd.* 7: 111–120, 1997). SP-A does not block transmembrane $Ca^{2+}$ fluxes, whether active (i.e., via voltage or other gated channels) or passive (e.g., via Io). (Strayer, et al, *Rec. Signal Transd.* 7: 111–120, 1997).

Signaling Mechanisms in Surfactant Secretion

The signaling mechanisms that stimulate and inhibit surfactant secretion are not well understood. The diversity of secretagogues, some with different receptors, some without receptors, each with separate signaling pathways, greatly complicates the task of elucidating how surfactant secretion is triggered. (Chander and Fisher, *Am. J. Physiol.* 258: L241–253, 1990; Rotonda, et al, *Thromb. Haemost.* 78: 919–925, 1997). The nature of the signal that begins at the SP-A receptor (SPAR) and down-regulates surfactant secretion is even more obscure.

Adenosine binds $A_2$ purine receptors to activate adenylate cyclase via G protein-dependent pathways to produce cAMP. cAMP activates protein kinase A. Alpha-adrenergic agonists act similarly, though through different receptors. ATP binds $P_{2y}$ and $P_{2u}$ receptors to signal via G proteins to activate phospholipase $C_\beta$ (phosphoinositide-specific phospholipase C, $PLC_\beta$). $PLC_\beta$ hydrolyzes phosphatidylinositol-3,4,5-trisphosphate to diacyl glycerol (DAG) and inositol-3,4,5-trisphosphate, both of which activate other enzymes, such as protein kinases C, phospholipase D, etc. Secretagogue-induced signaling in type II cells downstream from these points is poorly understood.

Intracellular calcium stores in different cell types possess several types of receptors that can be stimulated to cause $Ca^{2+}$ release. (Berridge, M J. *Nature* 361:315–325, 1993; Mikoshiba, K., *Curr. Opin. Neurobiol.* 7:339–345, 1997). Ryanodine and IP3 receptors (IP3R) are examples of proteins that traverse the ER membrane and release $Ca^{2+}$ on binding their ligands. Calcium release (or increased $[Ca^{2+}]_i$) may activate tyrosine-specific protein kinases and calmodulin-dependent kinases. (Sugden, et al, *Cell. Signal.* 9:337–351, 1997). Again, however, the means by which this signaling mechanism would result in surfactant secretion is unclear.

Downstream signaling that follows calcium release from stores is an area of intense investigation. In type II cells, calcium release activates cell membrane calcium channels, allowing influx of $Ca^{2+}$. (Berridge, M J, *Nature* 361:315–325, 1993; Putney, J W, Jr., *Science*, 262: 676–678, 1993; Putney, J W, Jr., *Cell*, 75, 199–201, 1993). The nature of the stimulus/stimuli that opens $Ca^{2+}$ channels is under debate. Candidates range from increased $[Ca^{2+}]_i$ to poorly characterized substances that may be released simultaneously with $Ca^{2+}$ from those stores. (Berridge, M J, *Nature* 361:315–325, 1993).

Surfactant Deficiency

Surfactant is essential for normal respiratory function. Diseases of surfactant deficiency are characterized by respiratory distress. Thus, when insufficient surfactant is present to lower surface tension, a great deal of energy is needed to reinflate alveoli. Consequently, inhalation causes damage to the alveolar lining cells (mainly type I pneumocytes). Surfactant insufficiency, whether due to prematurity, inactivation or genetic deficiency, is not compatible with extrauterine life. (Avery, et al, *AM. J. Dis. Child.* 97: 517–523. 1959; Lewis, et al., *Am. Rev. Resp. Dis.* 147: 218–233, 1993; Nogee, et al, *J. Clin. Invest.* 93: 1860–1863, 1994).

Pulmonary immaturity, termed neonatal respiratory distress syndrome (RDS) is a disease that occurs in infants born prematurely. It occurs in about 10,000 infants yearly in the U.S. In many such infants, their type II cell surfactant secretory apparatus has not matured adequately to sustain the levels of surfactant secretion needed for extrauterine life. The level of surfactant production, i.e., the level of pulmonary maturity at which extrauterine life can be sustained, has decreased greatly in recent years with improved ventilatory technology. The development of exogenous surfactant replacement therapy in such infants has provided an additional type of therapeutic intervention that has decreased both morbidity and mortality of neonatal RDS greatly. Currently, with surfactant replacement therapy and modem ventilatory techniques the mortality from neonatal RDS in infants who are born 26–28 weeks is less than 20%, and in some centers as low as 10%.

Unfortunately, surfactant replacement therapy is expensive. One dose for a 750 to 1000 gram infant costs about $1200, although the individual cost varies with the specific formulation. Many infants require more than one dose. Further, surfactant replacement therapy fails for unknown reasons in about 20% of premature infants in whom it is used.

Surfactant deficiency that is acquired may occur at any time in life, but generally involves adults. Statistics on its frequency are difficult to obtain because these patients are often classified according to initial extrapulmonary diseases (e.g., automobile accidents). Still, about 50,000 adult respiratory deficiency syndrome (ARDS) cases occur in the U.S. yearly.

This deficiency is a relative deficiency. Type II cells are mature, and are generally metabolically active and capable of producing and secreting surfactant. In ARDS, however, the alveolar space may contain inhibitors of surfactant function that, even in the presence of normal concentrations of surfactant, impede the surface activity of the lung's secreted surfactant. The surfactant inhibitors are usually considered to be natural plasma proteins that do not normally reach the air spaces of the lung, for example fibrinogen and albumin. Occasionally, in the setting of infection, microbial inhibitors of surfactant may also be involved.

Adult respiratory distress syndrome (ARDS) is a complex syndrome often involving substantial extrapulmonary disease. Pulmonary disease commonly represents one of a number of major organ system failures. ARDS may occur in the setting including, but not limited to, sepsis (i.e., overwhelming bacterial infection), traumatic shock (i.e., insufficient blood volume to maintain normal organ function, as can occur after an automobile accident), cardiogenic shock (heart failure), toxin exposure either by inhalation or other routes, and numerous other insults including fresh water drowning, severe radiation exposure, pneumonia, etc.

ARDS does not occur in all people exposed to these injuries. The reasons ARDS occurs in some and not others is unclear. The mortality of ARDS in the U.S. is about 50–60%, and has not changed greatly since the syndrome was first recognized in the early 1970s. Patients often die from their extrapulmonary diseases (e.g., overwhelming infection).

Treatment for ARDS is not very effective, and has not improved mortality greatly despite improved ventilatory therapy. This reflects in part the general complexity of these patients' clinical situations and in part the unavailability of surfactant replacement for ARDS patients. As indicated above, one dose of, for example, bovine surfactant for a 750 gram infant costs over $1000. A 75 kilogram adult would need at least 100× as much, and may well require several doses. While anecdotal reports in a small series of patients suggest that surfactant administration is helpful in ARDS, both availability and cost are major concerns.

To date, genetic deficiency of one of the surfactant proteins, surfactant protein B (SP-13) has been described in a small but growing population of infants. This disease is invariably fatal unless a lung transplant is performed in the neonatal period.

Given the high cost and lack of adequate therapies in the current protocols for treating a respiratory distress syndrome, there is a long felt, yet unfulfilled need, for additional therapies for respiratory distress. The present invention fulfills this need. The present invention examines the role of $Ca^{2+}$ in signaling surfactant secretion. The results imply that a novel role for calcium stores in cellular activation exists in type II alveolar pneumocytes.

BAPTA-AM, an esterified EGTA analogue, does not bind $Ca^{2+}$ and crosses cell membranes freely. It is de-esterified in the cytosol, whereupon it binds $Ca^{2+}$. BAPTA-AM causes a huge increase in surfactant secretion. It is non-toxic and commonly available. The present invention relates to the chelation of intracellular calcium, with for example BAPTA-AM, and to the stimulation of surfactant secretion by type II cells. The present invention is a major advance in pulmonary therapeutics. For a tiny fraction (<1%) of the cost of administering exogenous surfactant to a patient, the calcium chelator, for example BAPTA-AM, is instilled via a number of potential delivery mechanisms and will cause type II cells to release stored surfactant pools. Thus, the present invention provides a therapeutic/prophylactic method of treating a patient with a calcium chelator, thereby stimulating surfactant secretion by type II pneumocytes and facilitating a normal breathing pattern.

SUMMARY OF THE INVENTION

An object of the invention is to present a method of treating or preventing a respiratory distress syndrome in a mammal by administering a therapeutically effect amount of an agent that activates surfactant secretion in the mammal.

It is a further object of the present invention that the therapeutic agent used in the method of treatment or prevention of a respiratory distress syndrome uses at least one intracellular calcium chelator. In one embodiment of the invention the intracellular calcium chelator is BAPTA-AM. The BAPTA-AM is between 25 and 100 $\mu$M.

It is another object of the present invention that the therapeutic agent used in the method of treatment or prevention of a respiratory distress syndrome enhances secretion of surfactant from type II pneumocytes. In one embodiment the therapeutic agent acts by altering the endoplasmic reticulum free calcium concentration ($[Ca^{+2}]_l$) in the type II pneumocytes.

It is also an object of the present invention that the therapeutic agent is administered by aerosol, nebulization or liquid instillation.

P<0.05, compared to both +Ca group, and compared to o/n −Ca, Ca added back next day group. (actual values: for −Ca vs. +Ca: Io, P=0.0016; for TG, P=0.029; for −Ca compared to −Ca with calcium added back the next day P=0.037 for Io; P=0.016 for TG). For ATP, the difference between +Ca throughout and −Ca throughout is significant (P<10$^{-4}$) ND=not done. For PMA, the difference between the −Ca and the +Ca groups was not statistically significant (P=0.26), while that between the −Ca group and the group in which Ca2+ was added back was not significant (P=0.11).

Figure 2:
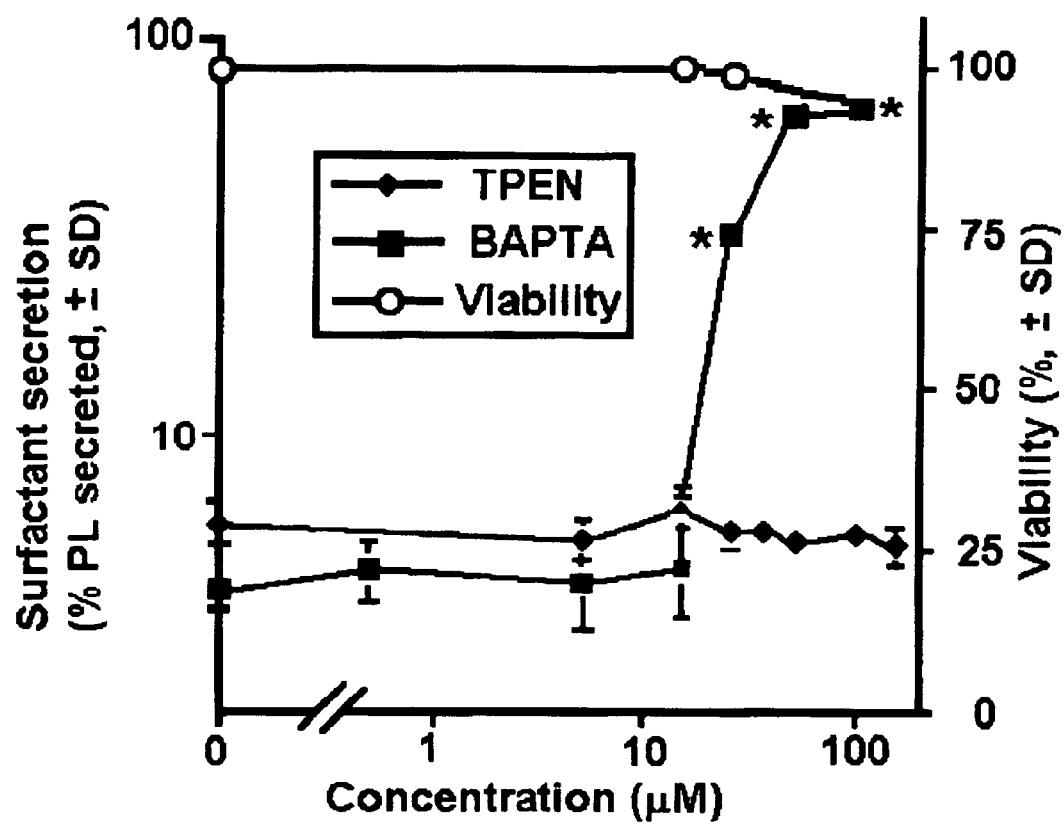

FIG. 2. Effects of BAPTA and TPEN on surfactant secretion by type II cells. Type II cells were isolated (infra) for standard surfactant secretion assays. To these cultures, different concentrations of BAPTA (■) and TPEN (♦) were added, and surfactant secretion was measured as percentage of $^3$H-labeled phospholipid secreted±S.D. (infra). Viability of type II cells (○) was measured by the method of Cory et al. (Cory, et al, *Cancer Comm.* 3: 207–212, 1991) in BAPTA-AM-treated cultures and is shown as a function of BAPTA concentration.

P<0.001, compared to untreated controls and compared to TPEN-treated cultures.

Figure 3:
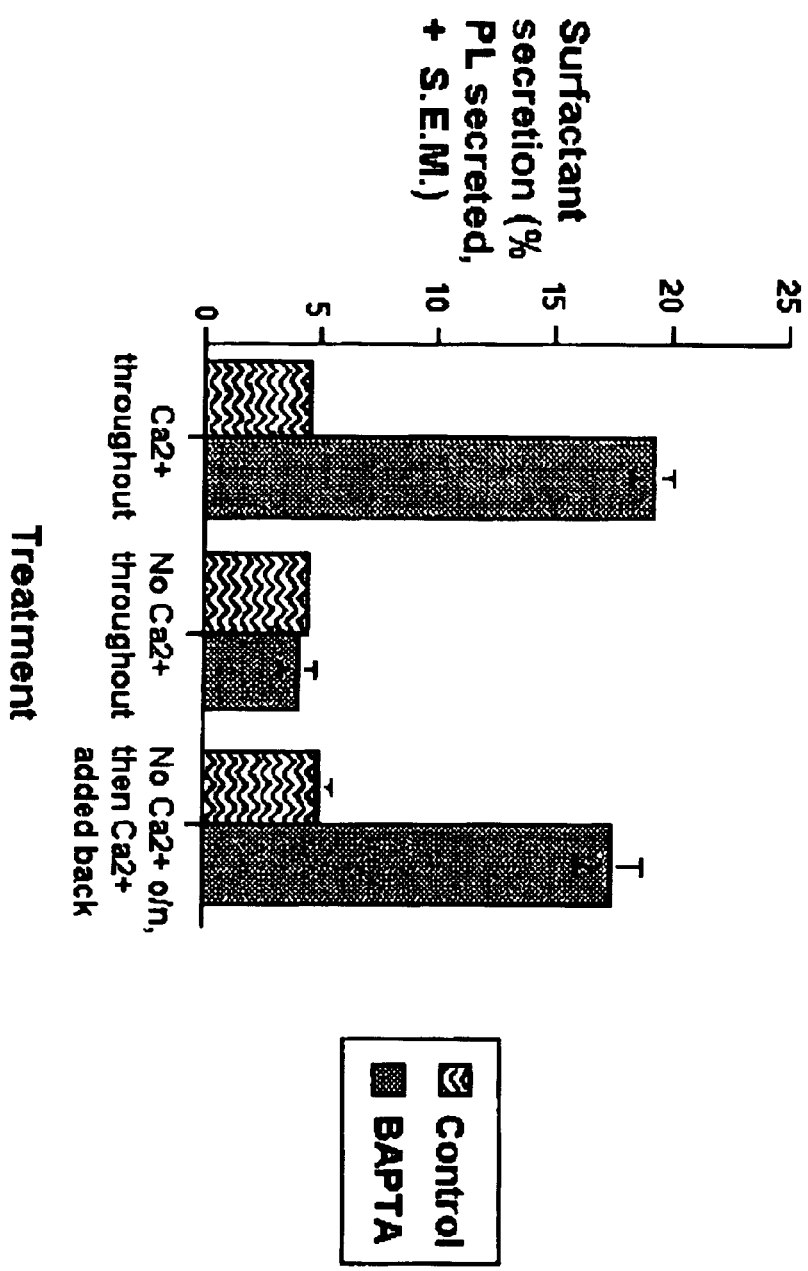

FIG. 3. BAPTA-induced surfactant secretion is inhibited by depleting cells of calcium and restored by adding calcium back. Type II cells were isolated (infra) for standard surfactant secretion assays. Cultures were maintained under three conditions: (i) at normal calcium concentration (1.64 mM) throughout the study (Ca$^{2+}$ throughout); (ii) totally without calcium (No −Ca$^{2+}$ throughout); or (iii) without calcium overnight to deplete cytosol Ca$^{2+}$ stores, but with Ca$^{2+}$ added back to 1.64 mM at the start of the 2 hr. secretion assay. To these cultures, BAPTA-AM (25 $\mu$M, grey columns) was added, with or without SP-A (100 ng/ml), and surfactant secretion was measured as percentage of $^3$H-labeled phospholipid secreted±S.E.M. (infra). Surfactant secretion was significantly different for cultures receiving BAPTA vs. controls (wavy hatched columns) when cells were exposed to calcium throughout, or when calcium was added back after overnight calcium depletion: P=0.0001 and P=0.0004 respectively. Surfactant secretion was not significantly different in BAPTA-AM-treated vs. control cultures incubated totally without calcium (P=0.496).

Figure 4:
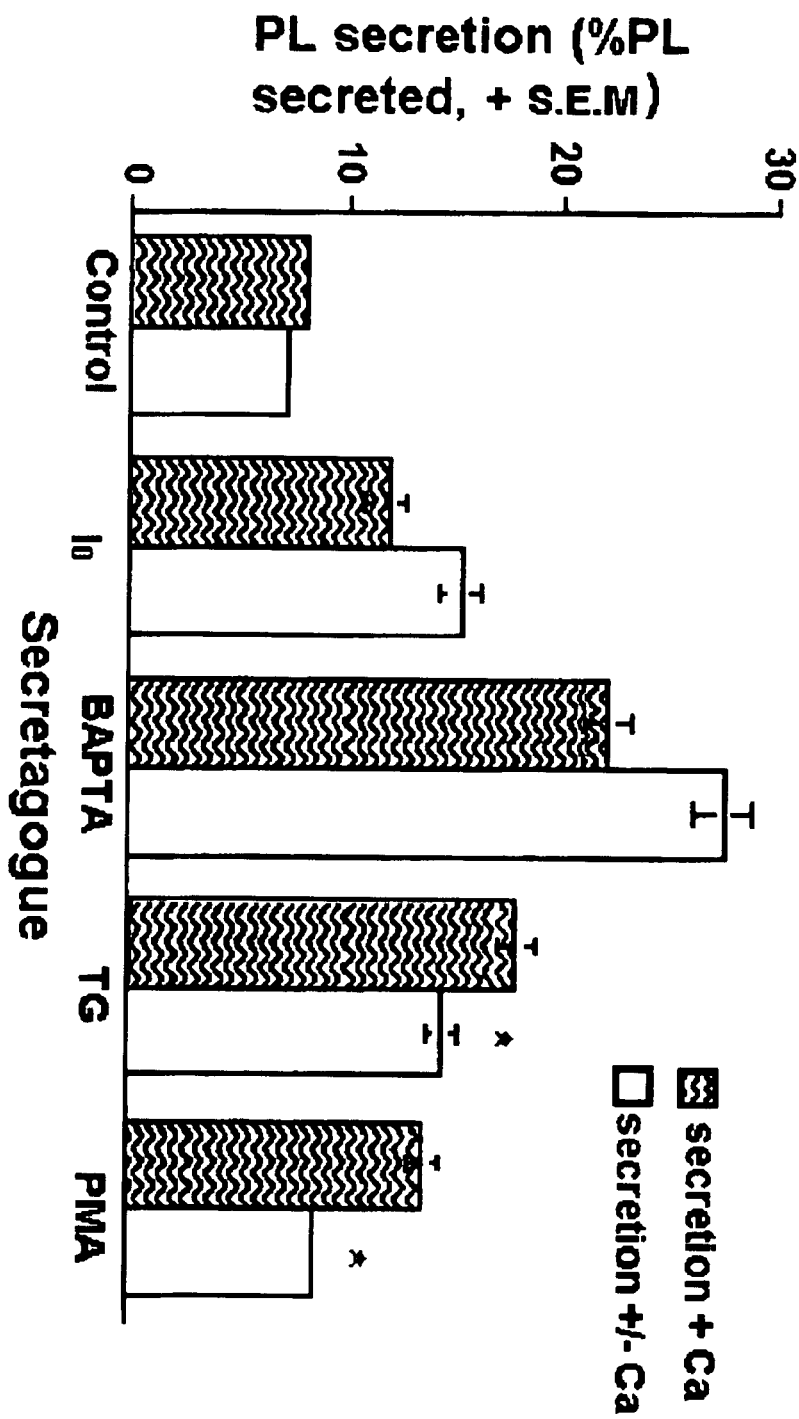

FIG. 4. Effects of short-term removal of calcium from the culture medium on surfactant secretion by type II cells. Type II cells were isolated as indicated (infra) for surfactant secretion assays. To these cultures, different secretagogues were added, and cells cultured overnight normally. For the 2 h secretion assay, cells were exposed to one of the several secretagogues listed, either with or without calcium in the medium for the 2 h assay period. Surfactant secretion was measured as percentage of $^3$H-labeled phospholipid secreted ±S.E.M. (infra). Differences in surfactant secretion between cells cultured in normal medium throughout (wavy hatched columns) and cells cultured overnight with normal medium, followed by 2 h in calcium-free medium during the assay (white columns) were not significant for control groups or for Io or BAPTA experimental groups.

P=0.03 comparing +Ca with +/−Ca groups, by Wilcoxson signed rank test.

Figure 5:
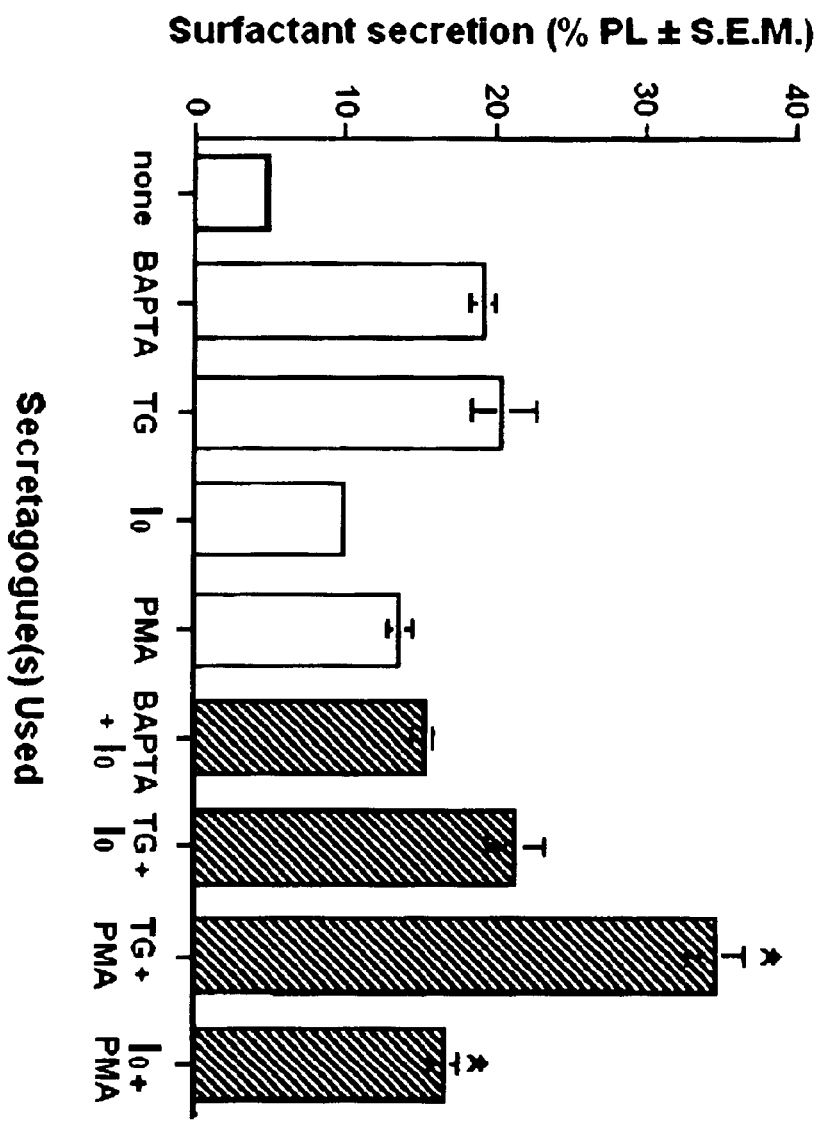

FIG. 5. Surfactant secretion in response to combinations of secretagogues. Type II cells were isolated, surfactant phospholipids labeled, and surfactant secretion assayed (infra). To these cultures, BAPTA, Io, TG, and PMA were added. These secretagogues were added alone or in combination. Type II cells cultured with some combinations of secretagogues (BAPTA+PMA, BAPTA+TG) did not survive the assay period; results shown are for those cultures in which viability exceeded 95% of originally plated cells.

P<0.05, compared to either secretagogue individually.

Figure 6A:
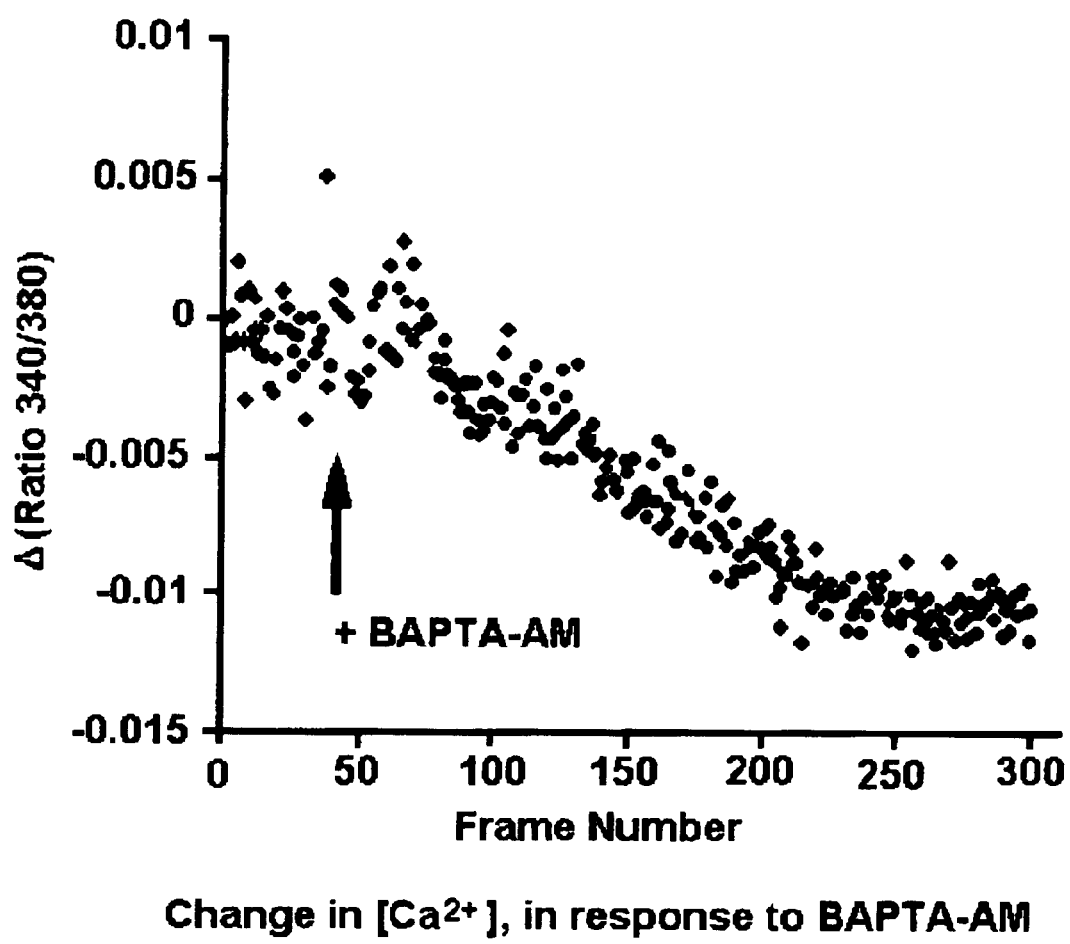
Figure 6B:
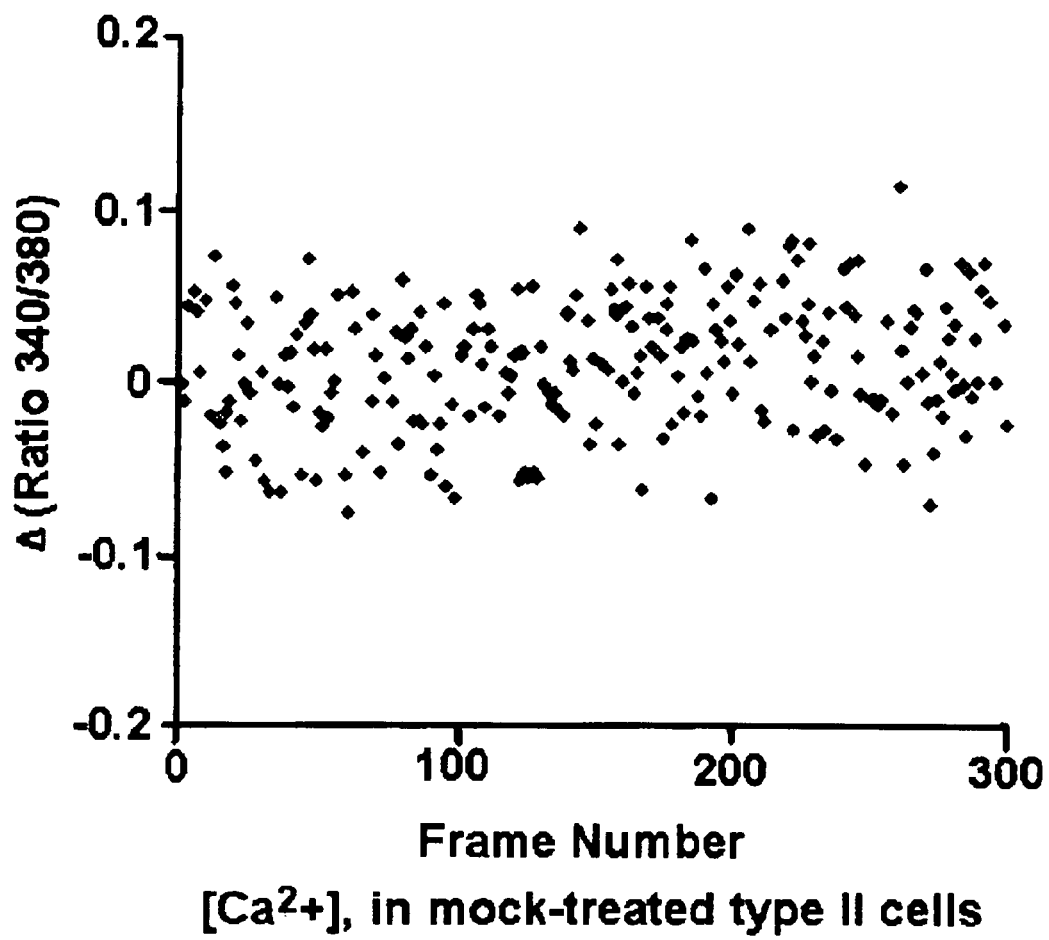
Figure 7A:
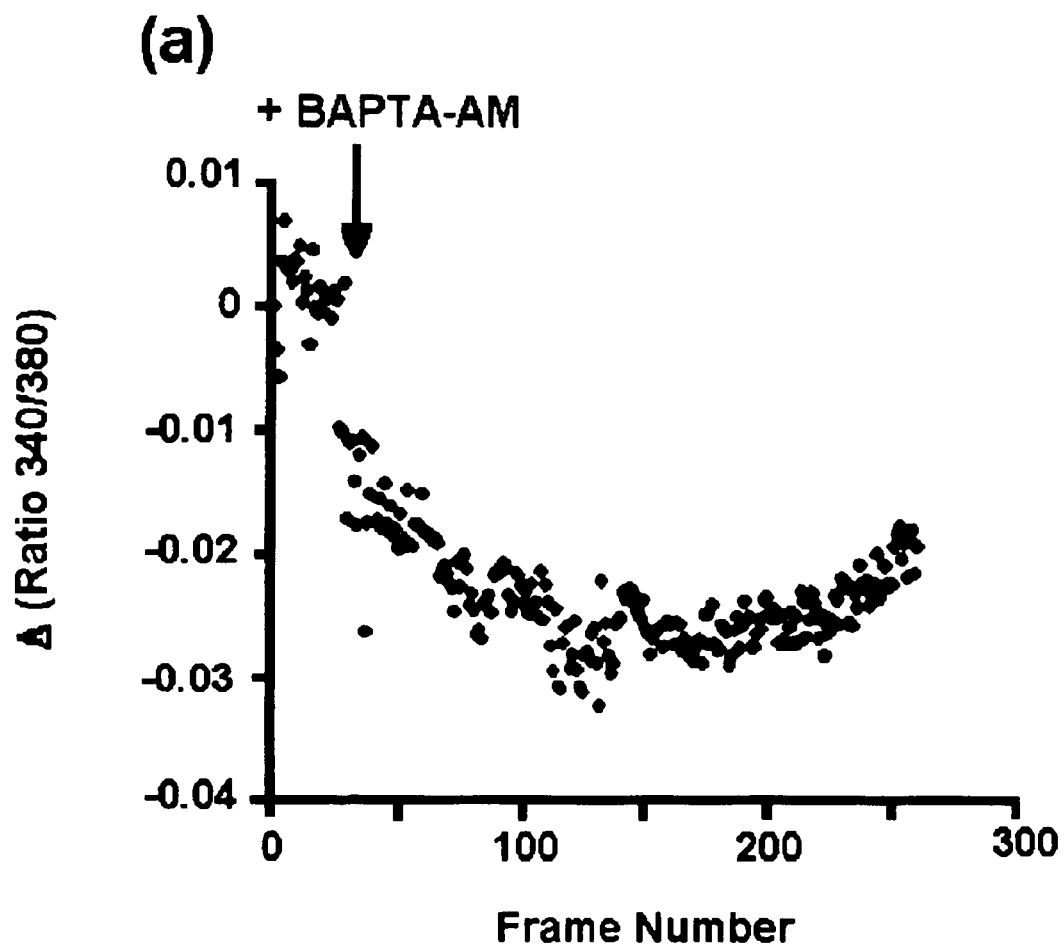
Figure 7B:
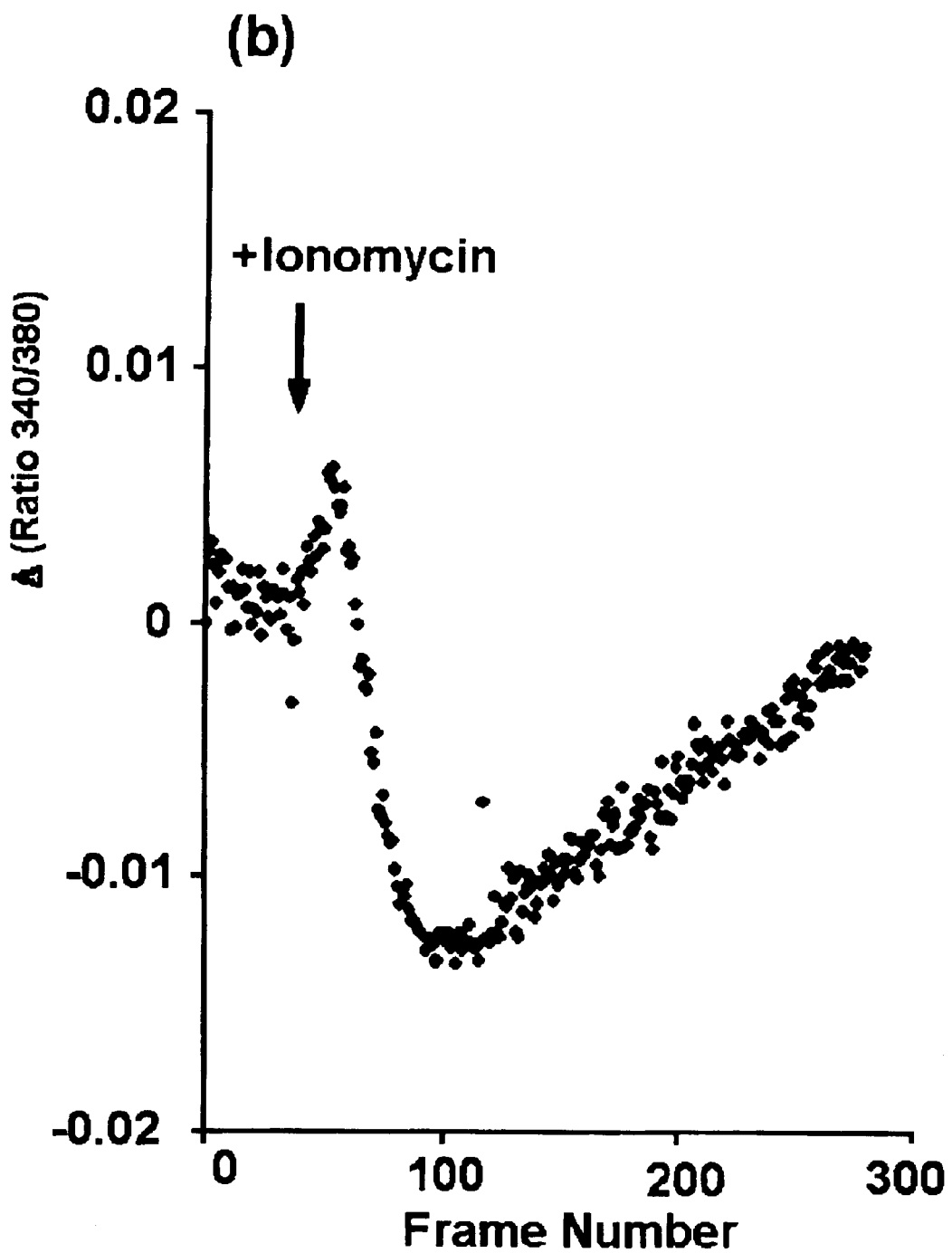
Figure 7C:
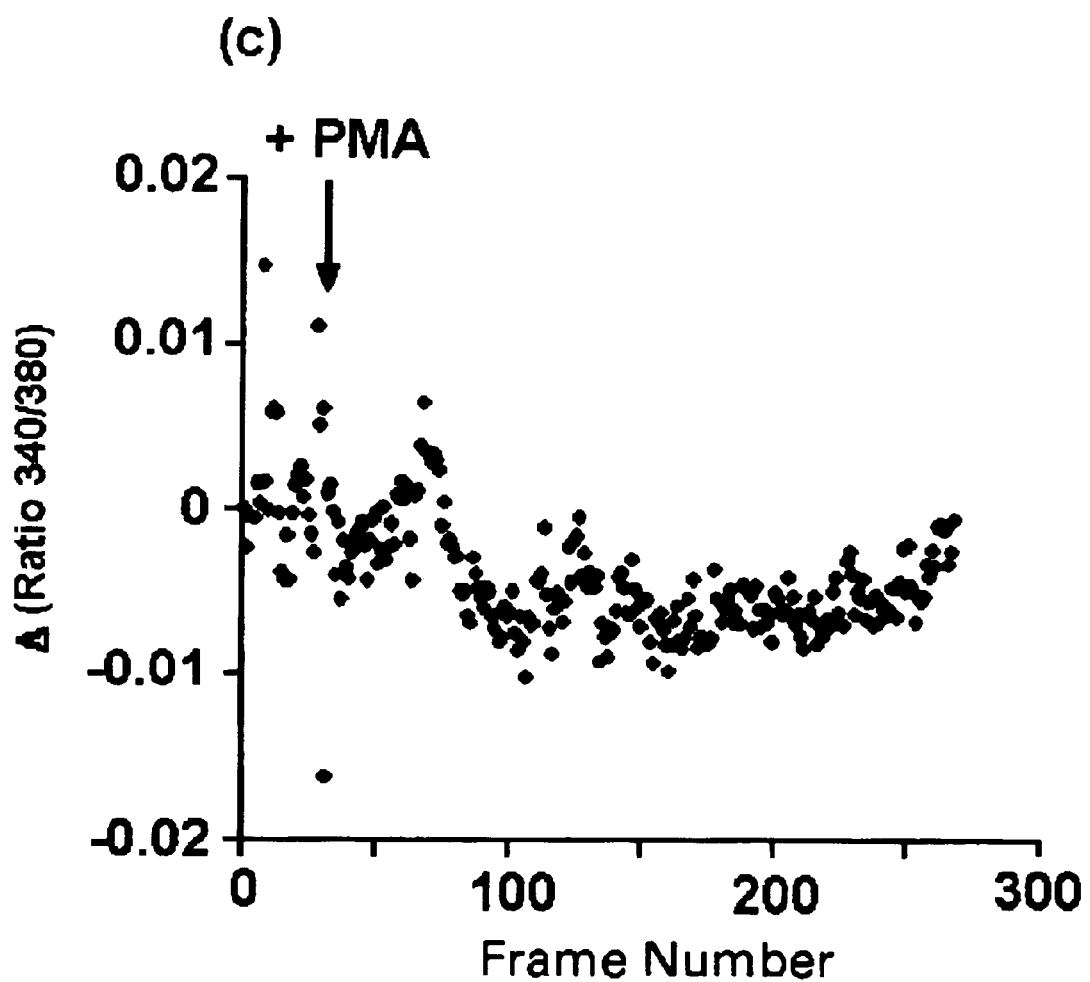
Figure 7D:
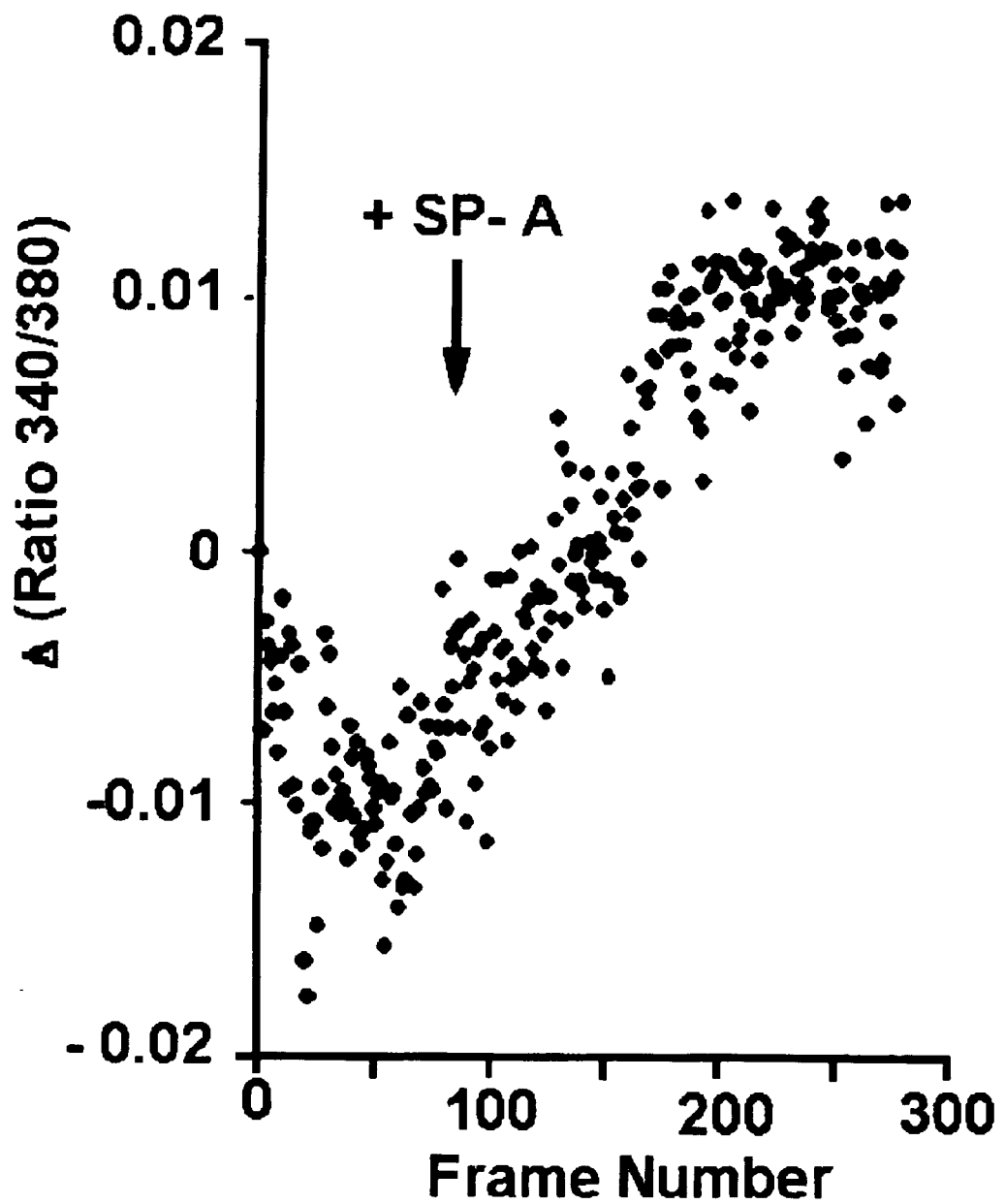
Figure 7E:
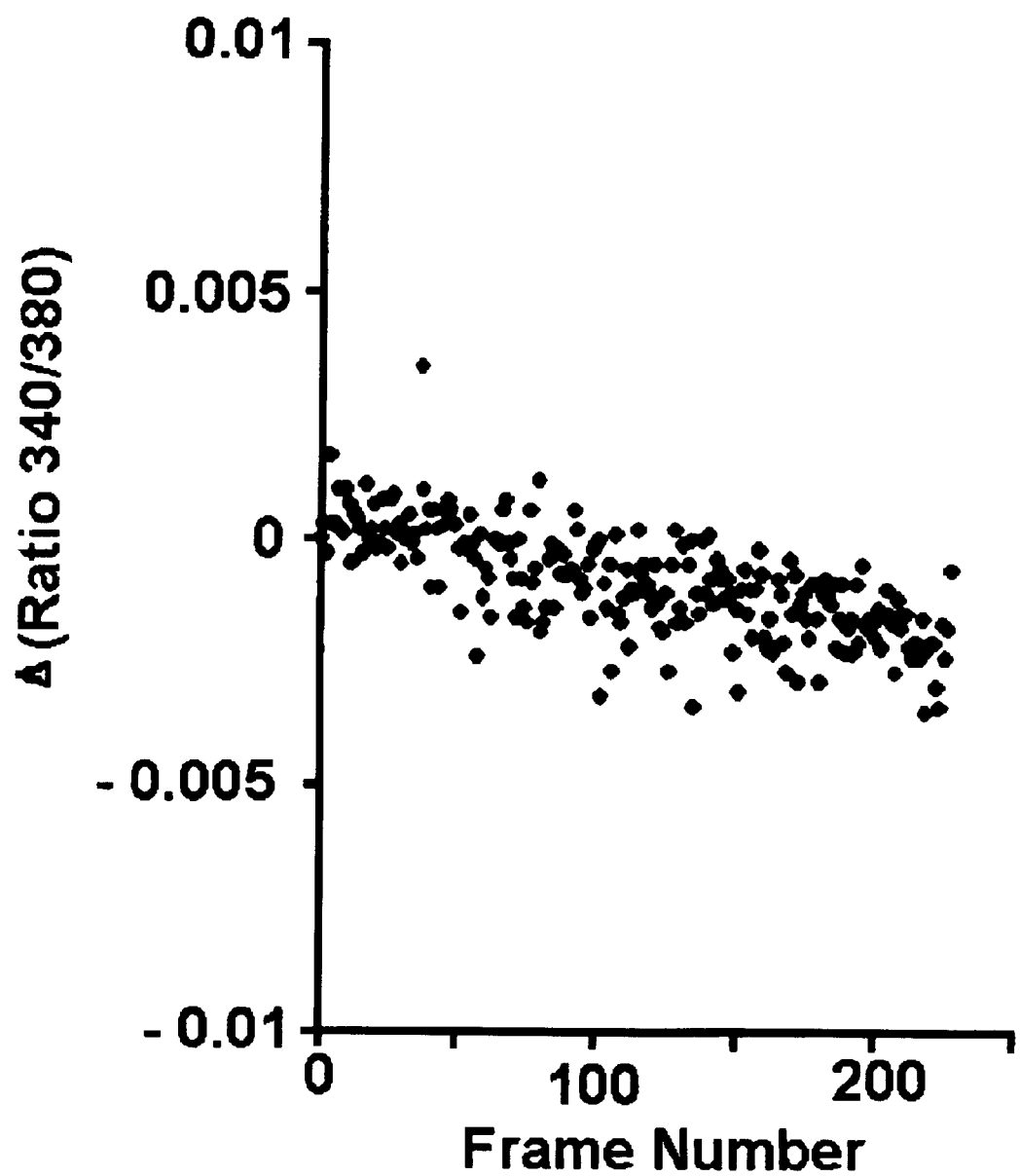

FIG. 6. Effect of BAPTA on cytosol free calcium concentration. Changes in cytosol calcium concentration were visualized from the ratio of fura2 fluorescence induced at 340 nm (fura2 bound to calcium), compared to that induced at 380 nm (unbound) (infra). In these representative tracings, cells were preloaded with fura2, BAPTA was added at the time indicated (a), or cells were untreated (b).

FIG. 7. Effects of BAPTA and other secretagogues, as well as SP-A, on lumenal calcium concentration. Changes in calcium levels within ER stores were visualized from the ratio of fura2ff fluorescence induced at 340 nm (fura2ff bound to calcium), compared to that induced at 380 nm (unbound) (infra). In these representative tracings, cells were preloaded with fura2ff, followed by $MnCl_2$ added at time=0. (Renard-Rooney, D. C., et al., *J. Biol. Chem.*, 268: 23601–23610, 1993). Additions were made at the indicated times: (a) BAPTA-AM; (b) Io; (c) PMA; (d) SP-A; (e) mock.

ABBREVIATIONS

"BAPTA-AM" is 1,2-bis(2-aminophenoxy)ethane-N,N,N,N-tetraacetic acid acetoxymethyl ester. This esterified form of the compound is the form that is placed in the culture medium in order to load the cells with this chelator.

"BAPTA" is 1,2-bis(2-aminophenoxy)ethane-N,N,N,N-tetraacetic acid. This form of the compound is the intracellular chelator.

"$[Ca^{2+}]$" is calcium concentration.

"$[Ca^{2+}]_c$" iscytosol free calcium concentration.

"$[Ca^{2+}]_l$" is free $[Ca^{2+}]$ in ER stores (lumenal).

"DPPC" is dipalmitoyl phosphatidylcholine.

"ER" is endoplasmic reticulum.

"Io" is ionomycin.

"IP3" is inositol trisphosphate.

"IP3R" is inositol trisphosphate receptor.

"MEM" is Modified Eagle's medium.

"PKA" is protein kinase A.

"PKC" is protein kinase C.

"PL" is phospholipid.

"PLC" is phospholipase C.

"PMA" is phorbol 12-myristate 13-acetate.

"PPI-PLCβ" is phosphatidylinositol phosphate-phospholipase Cβ.

"SP-A" is surfactant-associated protein-A.

"SPAR" is SP-A receptor.

"TG" is thapsigargin.

"TPEN" is N,N,N',N'-tetrakis-(2-pyridylmethyl) ethylenediamine.

DESCRIPTION OF THE INVENTION

Methods

Animals

Specified-pathogen free, female Sprague-Dawley rats (180–200 g) were purchased from Charles River Laboratories. The animals were used as sources of alveolar type II cells within 1 week of receipt.

Chemicals and Reagents

SP-A from bovine lung was purified and analyzed as described. (Dobbs, et al, *AM. Rev. Respir. Dis.* 134, 141–145, 1986). BAPTA AM and TPEN were purchased from Molecular Probes, Inc. (Corvallis, Oreg.). After initial dose-response studies, 25 µM BAPTA-AM was used to load type II cells.

Type II Cell Cultures

Freshly isolated type II cells were prepared according to standard techniques, originally described by Dobbs (Dobbs, et al, *AM. Rev. Respir. Dis.* 134, 141–145, 1986), and later modified by Sen and Chander (Sen and Chander, *Biochem. J.* 298: 681–687, 1994). The use of these techniques has been previously reported. (Strayer, et al, *Ex. Cell Res.* 226: 90–97, 1996; Strayer, et al, *Rec. Signal Transd.* 7: 111–120, 1997). Briefly, lungs of anesthetized rats were cleared of blood and treated with elastase endotracheally (Worthington Biochemical, Freehold, N.J.) to obtain free cells. The cells were separated from lung debris and plated on bacteriological plates coated with normal rat IgG (Sigma Chemical Co., St. Louis, Mo.). After 1 hr, free cells were collected by panning, pelleted, and resuspended ($0.8 \times 10^6$ cells/ml) in minimum essential medium (MEM)+10% fetal bovine serum (FCS, Life Technologies, Gaithersburg, Md.).

Secretion Studies

Secretion studies were performed as described by Sen and Chander. (Sen and Chander, *Biochem. J.* 298: 681–687, 1994). Briefly, $0.8 \times 10^6$ alveolar type II cells were cultured for 18 h in MEM with 10% FBS+0.5 µCi of [methyl-$^3$H]-choline (Amersham, Arlington Heights, Ill.) to label cellular phospholipids (PL) metabolically. Cells were washed to remove non-adherent cells and unincorporated radioactivity. After replacing this medium with fresh MEM, plates were incubated for 15 min. SP-A (100 ng/ml) was added to selected plates, followed by incubation for an additional 15 min.; secretagogues were then added at the appropriate concentrations [control (no addition), ATP (500 µM), TG (10 µM), ionomycin (1 µM), PMA (50 ng/ml)]. At this point (t=0) in each experiment, some samples were removed for analysis of secreted labeled lipids to establish a baseline. Incubation proceeded for an additional 2 h for all other plates. Following this incubation, media were removed and centrifuged (15 min., 300×g) to pellet cells that detached during incubation. These cells were later pooled with those recovered from the plates. Lipids from both media and plates were extracted (Sen and Chander, *Biochem. J.* 298: 681–687, 1994) after adding [methyl-$^{14}$C]-DPPC (Amersham, Arlington Heights, Ill.) as a recovery standard, and egg phosphatidylcholine (Sigma Chemical Co., St. Louis, Mo.) as a carrier lipid. Recovered lipids were dissolved in Scintiverse II fluid (Fisher Scientific, Pittsburgh, Pa.) and the radioactivity of these lipid extracts measured with a scintillation counter (Beckman Instruments, Fullerton, Calif.). $^3$H-labeled phospholipid recovery was normalized to recovery of [methyl-$^{14}$C]-DPPC. Phospholipid secretion was determined as percent secretion=(cpm in lipids recovered from media×100)/(cpm in lipids recovered from media and plates).

In some studies involving the effect of calcium depletion on phospholipid synthesis, synthesis of glycerol-based lipids was also measured by quantitating the incorporation of $^3$H-glycerol into surfactant lipids. Cell culture and lipid extraction were performed similarly to those described above except that [1,2,3-$^3$H]-glycerol (NEN Life Science Products, Inc., Boston, Mass.) was used instead of [methyl-$^3$H]choline.

Type II Cell Viability Assays

Viability of type II cells was tested both by trypan blue exclusion, and by tetrazolium/formazan assay (Promega Corp., Madison, Wis.), which measures mitochondrial dehydrogenases. These enzymes are only present in active form in living cells and are absent in nonviable cells. (Cory, et al, *Cancer Comm.* 3: 207–212, 1991). For such studies, an assay solution containing the tetrazolium compound (3-(4,5-dimethylthiazol-2-yl)-5-(3-carboxymethoxyphenyl)-2-(4-sulfonyl)-2H-tetrazolium, inner salt; MTS) and an electron-coupling reagent (phenazine methosulfate; PMS) in MEM is added to the cells. MTS is bioreduced by dehydrogenase enzymes found in metabolically active cells into a formazan compound that is soluble in tissue culture medium and directly measurable from its absorbance at 490 nm. Correction was made for the small effect of BAPTA itself on this reaction by running a parallel assay on plates with no cells.

Intracellular Calcium Measurements $10^6$ freshly isolated type II cells were added to 35 mm tissue culture plates, each containing a polylysine (Sigma Chemical Co.) coated 25 mm diameter coverslip and incubated (37° C., 5% $CO_2$) for at least 2 hr. Twenty min before use, Fura2/AM (Molecular Probes) was added (final concentration, 3 µM) to each coverslip. After Fura2 loading, the coverslips were washed with cell incubation buffer (121 mM NaCl, 4.7 mM KCl, 1.2 mM $KH_2PO_4$, 1.2 mM $MgSO_4$, 2 mM $CaCl_2$, 10 mM glucose, 5 mM $NaHCO_3$, 0.2% BSA, and 10 mM HEPES/NaOH, pH 7.4) and inserted into a thermostatically regulated chamber (37° C.). Cell incubation buffer was added and the whole assembly placed on the stage of a Nikon Diaphot inverted microscope. At appropriate times (see infra), secretagogues in the appropriate concentration (see supra) were added. Fluorescence images of the cells were collected by exciting the cells alternately at 340 and 380 nm and measuring emission at 500 nm using a charge-coupled device camera (Photometrics, Inc.) as described previously. (Rooney, et al, *Biol. Chem* 264: 17131–17141, 1989). Image acquisition and analysis were done with Macintosh computers running customized image-processing software. The ratio (340/380) of Fura2 excitation was calibrated to $[Ca^{2+}]_i$ as described. (Rooney, et al, *Biol. Chem* 264: 17131–17141, 1989; Grynkiewicz, et al, *J. Biol. Chem.* 260: 3440–3450, 1985).

ER Calcium Concentration

Type II cells were prepared as described and plated on glass coverslips that had been pretreated with poly-L-lysine (Sigma, 0.01%, 20° C., 15 mins). After incubation overnight at 37° C. in MEM-10% FCS, the cells were washed three times with serum-free MEM and once with loading buffer (121 mM NaCl, 4.7 mM KCl, 1.2 mM $KH_2PO_4$, 1.2 mM $MgSO_4$, 2% BSA, 10 mM glucose, 20 mM HEPES, 2 mM $CaCl_2$). The cells were loaded in loading buffer containing 10 µM Fura-2FF(AM) (Teflabs, Austin, Tex.) and 0.06% Pluronic Acid (Molecular Probes, Inc.) for two hours with shaking at 37° C. The coverslip was washed in calcium-free imaging buffer (121 mM NaCl, 4.7 mM KCl, 1.2 mM $KH_2PO_4$, 1.2 mM $MgSO_4$, 10 mM glucose, 20 mM HEPES), inserted into a thermostatically regulated chamber (37° C.), and mounted on an inverted fluorescence microscope in 1 ml of imaging buffer. Fluorescence imaging following excitation at 340 nm and 380 nm was performed (supra).

During imaging $MnCl_2$ was added at time=0 to a final concentration of 500 µM followed by either SP-A, ionomycin, or TG (final concentrations 100 ng/ml, 1 µM and 4 µM respectively).

Therapeutic Methods and Compositions

Therapeutic agent as used herein refers to an agent which is a biologically-active synthetic or natural substance, other than alveolar surfactant proteins themselves, that is useful for treating a medical or veterinary disorder or trauma, preventing a medical or veterinary disorder, or regulating the physiology of a human being or animal. Preferred pharmaceutical agents are those which are useful in treating disorders localized in or near the lungs or respiratory tract, including, but not limited to, infant or adult respiratory distress syndrome, oxygen toxicity associated with respirator therapy, pneumonia, bronchitis, asthma, emphysema, tuberculosis, chronic obstructive pulmonary disorders, and lung cancer.

"Respiratory distress syndrome" includes many conditions characterized by respiratory distress or failure. The following conditions represent some examples of respiratory distress or failure, but as this list is exemplary it is not intended to limit the use of the present invention: traumatic shock; Gram negative septic shock; sock due to other infectious organisms besides Gram negative bacteria; toxic shock; fluid loss or blood volume depletion other than traumatic shock; allergic reactions; allergic reactions to inhaled allergens; allergic reactions to ingested allergens; allergic reactions to administered allergens (either iatrogenically or otherwise); pneumonitis or pneumonia due to infectious agents; pneumonitis or pneumonia due to infectious agents where the infectious agent is bacterial; pneumonitis or pneumonia due to infectious agents where the infectious agent is fungal; pneumonitis or pneumonia due to infectious agent is a protozoan; pneumonitis or pneumonia due to infectious agents where the infectious agent is a multicellular organism; pneumonitis or pneumonia due to infectious agents where the infectious agent is mycoplasma; pneumonitis or pneumonia due to infecious agents where the infectious agent is Pneumocystis carinii; toxic pneumonitis; toxic pneumonitis where the toxin is inhaled; toxic pneumonitis where the toxin is ingested; toxic pneumonitis where the toxin is injected; toxic pneumonitis where the toxin is applied topically; primary organ failure in an organ other than the lungs; primary organ failure in an organ other than the lungs where that organ is the heart; primary organ failure in an organ other than the lungs where that organ is the liver; primary organ failure in an organ other than the lungs where that organ is the kidneys; primary organ failure in an organ other than the lungs where that organ is the digestive system; primary organ failure in an organ other than the lungs where that organ is the endocrine system (e.g., thyroid, adrenal, parathyroid); a reaction to an administered pharmacologic agent, including administered blood or blood products, pharmaceuticals and anesthetics; a tumor, benign or malignant, of the lungs or other organs; a developmental abnormality, including immaturity of the lungs; a developmental abnormality, including immaturity of the cardiovascular system; a developmental abnormality of the chest or chest wall; a developmental abnormality of the diaphragm; a developmental abnormality, including immaturity, of the digestive system; ionizing radiation.

The invention provides methods of treatment and prophylaxis by administration to a subject of an effective amount of a therapeutic, i.e., an intracellular calcium chelator. In a preferred aspect, the therapeutic is substantially purified. The subject is preferably an animal, including, but not limited to, animals such as cows, pigs, chickens, etc., and is preferably a mammal, and most preferably a human.

Various delivery systems are known and can be used to administer a therapeutic of the invention, e.g., encapsulation in liposomes, microparticles, microcapsules, expression by recombinant cells, receptor-mediated endocytosis (Wu and Wu, *J. Biol. Chem.* 262:4429–4432, 1987), construction of a therapeutic nucleic acid as part of a retroviral or other vector, etc.

The active compounds disclosed herein are administered to the lung(s) of a subject by any suitable means. Active compounds are preferably administered by administering an aerosol suspension of respirable particles comprised of the active compound or active compounds, which the subject inhales. The active compound can be aerosolized in a variety of forms, such as, but not limited to, dry powder inhalants, metered dose inhalants, or liquid/liquid suspensions. The respirable particles may be liquid or solid. The particles may optionally contain other therapeutic ingredients such as amiloride, benzamil or phenamil, with the selected compound included in an amount effective to inhibit the reabsorption of water from airway mucous secretions, as described in U.S. Pat. No. 4,501,729.

The particulate pharmaceutical composition may optionally be combined with a carrier to aid in dispersion or transport. A suitable carrier such as a sugar (i.e., lactose, sucrose, trehalose, mannitol) may be blended with the active compound or compounds in any suitable ratio (e.g., a 1 to 1 ratio by weight).

Particles comprised of the active compound for practicing the present invention should include particles of respirable size, that is, particles of a size sufficiently small to pass through the mouth or nose and larynx upon inhalation and into the bronchi and alveoli of the lungs. In general, particles ranging from about 1 to 10 microns in size (more particularly, less than about 5 microns in size) are respirable. Particles of non-respirable size which are included in the aerosol tend to deposit in the throat and be swallowed, and the quantity of non-respirable particles in the aerosol is preferably minimized. For nasal administration, a particle size in the range of 10–500 $\mu$m is preferred to ensure retention in the nasal cavity.

Liquid pharmaceutical compositions of active compound for producing an aerosol may be prepared by combining the active compound with a suitable vehicle, such as sterile pyrogen free water. The hypertonic saline solutions used to carry out the present invention are preferably sterile, pyrogen-free solutions, comprising from one to fifteen percent (by weight) of the physiologically acceptable salt, and more preferably from three to seven percent by weight of the physiologically acceptable salt.

Aerosols of liquid particles comprising the active compound may be produced by any suitable means, such as with a pressure-driven jet nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation.

Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic, but may be hypertonic with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate therapeutic aerosol generator. Aerosol generators for administering solid particulate therapeutics to a subject produce particles which are respirable and generate a volume of aerosol containing a predetermined metered dose of a therapeutic at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 200 $\mu$l, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidant and suitable flavoring agents.

The present invention considers the route of administration of the therapeutic agent, the amount of therapeutic agent delivered to the injured region of the lung and the length of time which the therapeutic agent is delivered to the injured region of the lung to be determined by the physician in a particular situation. In addition, the periodicity of the treatment and the number of treatments administered during each period is dependent on the condition of the patient and the response of that patient to the treatment.

Results

Phorbol Ester Treatment Does Not Alter Cytosol Calcium

The effect of the phorbol ester secretagogue, phorbol myristate acetate (PMA), on $[Ca^{2+}]_i$ was examined. The lack of alteration in $[Ca^{2+}]_i$ on PMA treatment of type II cells has been reported. (Sano, et al, *Am. J. Physiol.* 253: C679–C686, 1987; Pian, et al, *Biochim. Biophys. Acta* 960: 43–53, 1988). The effect of PMA on type II cell $[Ca^{2+}]_i$ was tested by digital imaging fluorescence microscopy, which confirmed that PMA did not alter $[Ca^{2+}]_i$ in type II cells.

Calcium Depletion Reduces Surfactant Secretion Induced by Io and TG, but Not by PMA ATP, terbutaline, Io and TG all elicit biphasic increases in $[Ca^{2+}]_i$, reflecting both calcium release and calcium influx. (Strayer, et al, *Rec. Signal Transd.* 7: 111–120, 1997). SP-A, acting through its type II cell membrane receptor, inhibits both the surfactant secretion and $Ca^{2+}$ transients stimulated by ATP, Io and TG (Strayer, et al, *Rec. Signal Transd.* 7: 111–120, 1997). PMA, in contrast, stimulates surfactant secretion without altering $[Ca^{2+}]_i$. To test whether secretion induced by these secretagogues required calcium signaling, secretagogue activities in $Ca^{2+}$-depleted type II cells was studied.

Type II cells were incubated overnight and loaded with a $^3$H-phospholipid (PL) precursor in $Ca^{2+}$-free medium. They were then treated with ATP, Io, TG or PMA, still in calcium-free medium, and PL secretion was measured 2 h later. Calcium depletion in this manner prevented PL secretion stimulated by ATP and Io, and partially inhibited that stimulated by TG. It did not alter PMA-stimulated surfactant secretion (FIG. 1).

An altered PL labeling due to the incubation of cells without $Ca^{2+}$ might account for the observed changes. Surfactanc secretion is expressed, relative to internal standards, as a percentage of total PL secreted in 2 h. Thus, altered labeling efficiency should not cause observed decreases in secretion in $Ca^{2+}$-depleted cells. To assess the effects of depleting cells of $Ca^{2+}$ on PL synthesis, labeled PL (cpm $^3$H-choline or $^3$H-glycerol incorporated into PL/0.8×$10^6$ cells) in type II cells that were cultured with and without $Ca^{2+}$ overnight were compared. Overnight culture without calcium did not affect PL synthesis (Table 1).

TABLE 1

Effect of calcium depletion on PL synthesis

| | Incorporation into PL (% control) Cells cultured overnight: | | |
|---|---|---|---|
| PL precursor used | +Ca$^{2+}$§ | −Ca$^{2+}$ | P* |
| [methyl-$^3$H]-choline | 100% ± 58% | 160.8% ± 38.5% | 0.210 |
| [1,2,3-$^3$H]-glycerol | 100% ± 12% | 93.0% ± 14.5% | 0.249 |

§Control groups
*P value, as determined by Wilcoxon Signed Rank Test
Type II cells were isolated as indicated (supra) for standard surfactant secretion assays, in which either [methyl-$^3$H]-choline or [1,2,3-$^3$H]-glycerol was used as the phospholipid precursor. Cells were cultured overnight with or without calcium in the tissue culture medium, and surfactant lipids extracted the following day. Incorporation of radiolabeled choline and glycerol into surfactant lipids is expressed as a percentage of the control (+ calcium), ± S.D.

Secretagogue Activity is Restored by Adding Calcium

Figure 1:
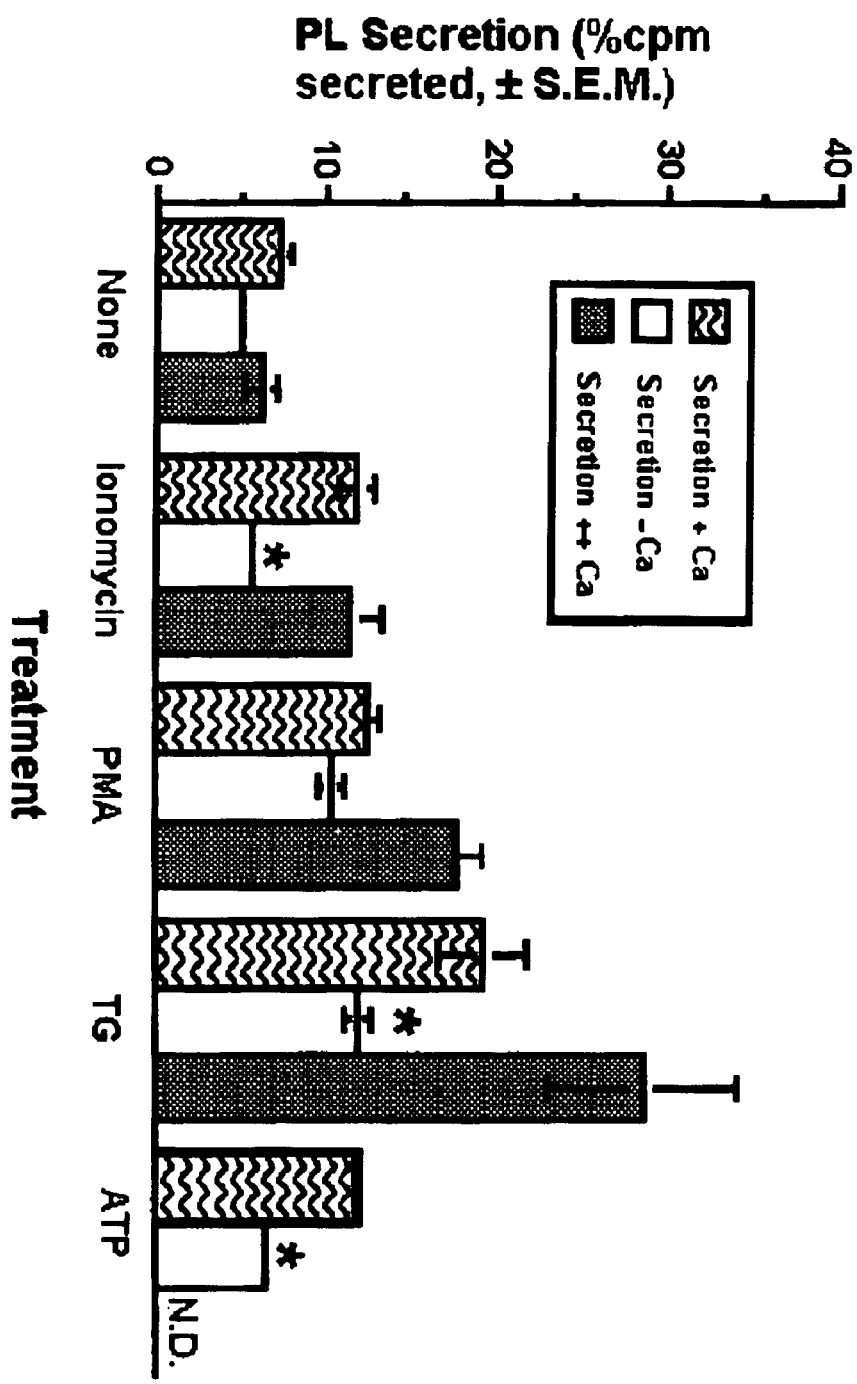
FIG. 1. Secretagogue-induced surfactant secretion with and without calcium. Type II cell secretion of $^3$H-labeled phospholipids (PL) was measured (infra) according to Dobbs (Dobbs, et al, *AM. Rev. Respir. Dis.* 134, 141–145, 1986) and Sen and Chander (Sen and Chander, *Biochem. J.* 298: 681–687, 1994). Cells were either cultured without added secretagogue, or with ATP, Ionomycin, PMA or thapsigargin (TG). Culture medium was maintained (i) with normal calcium concentration (1.64 mM) throughout the experiment (wavy hatched columns); (ii) without calcium throughout the experiment (white columns); or (iii) without calcium overnight to deplete cytosol calcium stores, but with calcium added back to its normal concentration in MEM (1.64 mM) at the start of the 2 hr. secretion assay (grey columns). Surfactant secretion is expressed as a percentage of total labeled phospholipids,±S.E.M. These data represent the average of 9 independent experiments.

The importance of calcium in the activity of these secretagogues was studied in Ca$^{2+}$-deprived cells by replenishing calcium, incubating the cells for 15 min., and then adding secretagogues (FIG. 1). Adding Ca$^{2+}$ back in this way restored PL secretion in response to Io and TG. Re-adding Ca$^{2+}$ also increased PMA-induced secretion, but this effect was not statistically significant.

Before adding secretagogues, $^3$H-choline-containing medium is removed and the cells are washed. An enhanced PL synthesis from the small pool of unincorporated $^3$H-choline within the cells might account for the apparent increased secretion during the 2 h between re-adding Ca$^{2+}$ and the assay. Therefore, the total $^3$H-PL after overnight incubation was compared to that after 2 additional hours of culture, both without secretagogue. The additional 2 h during the assay did not increase PL synthesis significantly (207,175±78,555 cpm overnight, vs. 203,554±73,101 cpm over-night+2 h; P=0.640 by Wilcoxson signed rank test).

Chelation of Intracellular Calcium Stimulates Surfactant Secretion

Ca$^{2+}$ depletion inhibits PL secretion that is induced by Ca$^{2+}$-releasing secretagogues (supra), and secretagogue activity is restored by re-adding Ca$^{2+}$. Secretagogue-induced changes in [Ca$^{2+}$]$_i$ is central to surfactant secretion, i.e., increased [Ca$^{2+}$]$_i$ due to release from ER stores could signal type II cell activation to secrete PL. Therefore, the effects of chelating calcium on surfactant secretion was tested. BAPTA-AM, an esterified EGTA analog, does not bind Ca$^{2+}$ and crosses cell membranes freely. It is de-esterified in the cytosol, whereupon it binds Ca$^{2+}$. If increases in [Ca$^{2+}$]$_i$ elicited by Ca$^{2+}$-releasing secretagogues is important in PL secretion, BAPTA should decrease surfactant secretion. However, the results reveal that BAPTA is a powerful secretagogue at concentrations between 25–100 μM (FIG. 2).

BAPTA chelates calcium and other cations. TPEN is a chelator of heavy metal cations. It crosses cell membranes but binds calcium much more weakly than BAPTA. To test whether chelation of other cations explains BAPTA secretagogue activity, TPEN was tested along with BAPTA. TPEN showed no secretagogue activity, even at 150 μM (FIG. 2).

BAPTA-AM is not known to be toxic to experimental animals or cells. In these studies, cellular viability was determined in two ways. Viable cells enumerated by counting trypan blue-excluding cells. Neither BAPTA-AM nor TPEN at these concentrations had any effect on cell viability, compared to each other or to cultures of untreated type II cells. In addition, cellular viability in BAPTA-AM-treated cultures was measured using the tetrazolium/formazan assay for mitochondrial dehydrogenase. (Cory, et al, *Cancer Comm.* 3: 207–212, 1991). These data, included in FIG. 2, also indicate that the viability of BAPTA-AM-treated type II cells does not differ from that of control cells.

Thus, BAPTA-AM, an inhibitor of cellular calcium and commercially available from chemical companies, does not inhibit surfactant secretion. This inhibitor causes a huge increase in surfactant secretion. This increased secretory activity is very large and highly reproducible. Within 4 hours of treatment, type II cells typically release about ⅔ of their stored surfactant, while control cells release about 7% in this time period.

BAPTA-induced PL Secretion is Inhibited by SP-A

SP-A inhibits secretagogue activities of ATP, Io and TG, all of which release Ca$^{2+}$ from ER stores (Strayer, et al, *Exp. Cell Res.* 226: 90–97, 1996; Strayer, et al, *Rec. Signal Transd.* 7: 111–120, 1997), as well as that of PMA, which does not alter [Ca$^{2+}$]$_i$ (Dorn, C C, et al., *Br. J. Pharmacol.*, 97:163–170, 1989; Kuroki, Y., et al., *Biochem. J.*, 115: 115–119, 1991). BAPTA is a powerful secretagogue that binds cytosol calcium, buffering [Ca$^{2+}$]$_i$. Analysis of whether SP-A altered BAPTA-induced surfactant secretion was determined. Type II cells were pretreated with SP-A, then exposed to BAPTA-AM (loading concentration, 25 μM). Following SP-A treatment, BAPTA induced significantly less surfactant secretion than in control cells that were not exposed to SP-A (Table 2).

TABLE 2

Effect of SP-A on BAPTA-induced surfactant secretion

| Treatment | % PL secreted | ±S.D. |
|---|---|---|
| No additions | 8.33 | 0.15 |
| +SP-A | 4.98 | 0.94 |
| +BAPTA-AM | 15.47 | 1.24 |
| +BAPTA-AM + SP-A | 12.98 | 0.61* |

Type II cells were isolated (supra) for standard surfactant secretion assays. To these cultures, BAPTA (25 μM) was added, with or without SP-A (100 ng/ml), and surfactant secretion was measured as percentage of $^3$H-labeled phospholipid secreted ± S.E.M., as described supra.
*P < 0.02, compared to cultures treated with BAPTA alone.

BAPTA Elicits Surfactant Secretion by Chelating Calcium

To ascertain that chelation of Ca$^{2+}$, and not other cations, was responsible for BAPTA secretagogue activity, type II cells were maintained in Ca$^{2+}$-free medium overnight, and then during and after treatment with BAPTA-AM (25 μM). Depleting cell Ca$^{2+}$ prevented BAPTA secretagogue activity (FIG. 3). Secretagogue activity was restored by re-adding calcium after overnight depletion. Thus, like secretagogues that release Ca$^{2+}$ from stores, BAPTA-induced surfactant secretion requires Ca$^{2+}$.

Calcium Influx is not Necessary for Secretagogue Activity

Calcium signaling in many cell types involves both release from stores and transmembrane influx. To test whether Ca$^{2+}$ influx is important in Ca$^{2+}$ signaling of surfactant secretion, type II cells were cultured in standard MEM containing 1.5 mM Ca$^{2+}$ overnight during PL labeling. This medium was exchanged for Ca$^{2+}$-free medium just before the addition of the secretagogues. Despite some variability, most likely due to assaying secretion in non-equilibrium conditions, when Ca$^{2+}$ influx is prevented, i.e., by removing extracellular Ca$^{2+}$ during the assay, the surfactant secretion elicited by BAPTA or Io is not significantly altered (FIG. 4). Statistically significant but small decreases in TG- and PMA-induced secretion were noted.

Secretagogue Activities of Calcium-releasing Secretagogues Are Not Additive, Except to that of PMA If the several secretagogues stimulate surfactant secretion via the same pathway, their activities should overlap and their secretagogue activities should not be additive. If, however, two secretagogues stimulate surfactant secretion via different pathways, surfactant secretion following treatment with both simultaneously may exceed that elicited by either alone. PMA induces surfactant secretion without increasing $[Ca^{2+}]_i$, even in calcium depleted cells. Its secretagogue activity could thus reflect a different signaling pathway or, less likely, action at a different point in the same pathway. Combinations of calcium-releasing secretagogues and PMA were tested for secretagogue activity. Adding two calcium-releasing secretagogues together did not increase surfactant secretion beyond that seen with either individually (FIG. 5). However, when PMA was added to a $Ca^{2+}$-releasing secretagogue, the observed secretagogue activities were additive.

Cell viability was measured in all studies. Some combinations of secretagogues-PMA+BAPTA and BAPTA+TG—were toxic to type II cells, thus the additivity of these secretagogue activities could not be assessed.

Effect of BAPTA on Cytosol Calcium Concentration

BAPTA, a calcium chelator, while requiring calcium to activate surfactant secretion, should not alter $[Ca^{2+}]_i$. To ascertain this, $[Ca^{2+}]_i$ was followed in type II cells loaded with fura2, and then exposed to BAPTA-AM. As measured by a decrease in the ratio of fura2 excitation at 340 nm compared to 380 nm, BAPTA-AM caused $[Ca^{2+}]_i$ to decrease somewhat, compared to mock-treated cells (FIG. 6). Thus, BAPTA-AM is a calcium dependent secretagogue that does not increase $[Ca^{2+}]_i$.

Alterations in Lumenal Calcium Concentration in Response to Calcium-releasing Secretagogues, PMA, BAPTA, and SP-A Decreases in $[Ca^{2+}]_l$, rather than increases in $[Ca^{2+}]_i$, were hypothesized to be the critical regulator of surfactant secretion by all secretagogues, with the exception of PMA. This theory predicts that BAPTA-AM, and other calcium-dependent secretagogues, would decrease $[Ca^{2+}]_l$, but that PMA would not. Thus, type II cells were loaded with fura2ff. This fluorophore has a much lower affinity for calcium in the $\mu$M range than fura2 does, and is therefore used to assess changes in $[Ca^{2+}]_l$. Type II cells were also treated with $Mn^{2+}$, which binds cytoplasmic fura2ff and prevents its binding to $Ca^{2+}$. (Dorn, et al, *Br. J. Pharmacol.* 97: 163–170, 1989; Kuroki, et al, *Biochem. J.* 115: 115–119, 1991; Miyata, et al, *Am. J. Physiol.* 261: H1123–H1134, 1991). Any changes in the lumenal free calcium concentration were measured as changes in the ratio of fura2ff excitation at 340 nm to that at 380 nm. As predicted, BAPTA decreased $[Ca^{2+}]_l$, as did Io (FIG. 7). PMA had no effect.

Effect of SP-A on Lumenal Calcium Concentration

To explain SP-A inhibition of both secretagogue-induced $Ca^{2+}$ release and secretagogue-induced surfactant secretion, SP-A was hypothesized to further increase the stores' avidity for calcium, increasing $Ca^{2+}$ uptake, and rendering lumenal $Ca^{2+}$ less susceptible to release. SP-A alone should then increase $[Ca^{2+}]_l$. This was tested as in type II cells loaded with fura2ff and treated with Mn2+(supra). SP-A caused increased $[Ca^{2+}]_l$ in Type II cells (FIG. 7).

Discussion

BAPTA Does Not Change $[Ca^{2+}]_i$

The essential nature of calcium signaling in surfactant secretion implies an important role for $[Ca^{2+}]_i$ in that signaling. The ability of BAPTA to stimulate surfactant secretion is key to understanding both signaling by $Ca^{2+}$-releasing secretagogues, and by $Ca^{2+}$ inhibition by SP-A.

The secretagogue activities of ATP, Io, and TG are all inhibited by depleting cytosol calcium, and are restored by replenishing calcium. PMA-stimulates secretion, which appears to circumvent calcium signaling in type II cells, and is not affected by depleting cytosol calcium.

TG-induced secretion is less completely inhibited by depleting cytosol $Ca^{2+}$ than is secretion induced by other calcium-releasing secretagogues. The reasons for this are not known. TG may, for example, access a store of calcium (such as high affinity binding sites) not easily depleted by overnight culture without $Ca^{2+}$, and not accessible to other secretagogues.

$Ca^{2+}$ influx is not a major participant in signaling surfactant secretion. When $Ca^{2+}$ is removed from the medium at assay time BAPTA- or Io-induced secretion are not affected. Small decreases in TG- and PMA-induced secretion seen in these studies are of borderline statistical significance (P=0.03).

Calcium starvation does not make surfactant totally unavailable for secretion, as PMA-induced secretion is largely unaffected. PL synthesis is unaffected, incorporation of choline and glycerol precursors into PL is similar in calcium-starved and control cells.

In this regard the ability of a cation chelator, BAPTA, to stimulate type II cells to secrete surfactant is illuminating. The cation involved in BAPTA-induced secretion is calcium. TPEN, which chelates transition metals like iron, zinc, etc. well, and $Ca^{2+}$ poorly (Aballay, et al, *Biochem. J.* 312: 919–23, 1995; Richardson, et al, *J. Biol. Chem.* 268: 11528–11533, 1993), does not stimulate surfactant secretion. More importantly, BAPTA secretagogue activity is eliminated by depleting $Ca^{2+}$ and restored by replacing it. Another group reported using BAPTA in type II cell cultures, but at 5 $\mu$M. (Benito, et al, *Mol. Cell. Biochem.* 189: 169–176, 1998). In the present invention, the dose-response studies in the concentration range of 5 $\mu$M are below the threshold for BAPTA to stimulate surfactant secretion. Stimulation of surfactant secretion with BAPTA occurs between 25–100 $\mu$M.

The ability of BAPTA to stimulate secretion does not involve depleting the total cellular pool of calcium, as overnight $Ca^{2+}$ deprivation itself does not elicit large-scale surfactant secretion. There are several possible explanations for these findings. As in other systems (Lillie, et al *Phil. Trans. Royal Soc. Lond. Ser. B.* 336: 25–34, 1992; Lillie, et al, *Biochem. J.* 288: 181–187, 1992), $Ca^{2+}$ is needed further downstream for surfactant secretion, independently of signaling. BAPTA buffering cellular $Ca^{2+}$ does not block such a calcium-requiring step, while depleting cellular calcium does. Calcium also helps to maintain the structure of ER stores, and its depletion will distort these stores and render them less effective in transducing secretion-activating signals. (Blatter and Weir, *Biophys. J.* 58: 1491–1499, 1990).

From the perspective of Type II cell surfactant secretion, BAPTA-AM acts like a $Ca^{2+}$-releasing secretagogue. It causes surfactant secretion in a dose-dependent manner; is inhibited by depleting calcium; does not require calcium influx; and is inhibited by SP-A. However, unlike calcium-releasing secretagogues, BAPTA does not raise $[Ca^{2+}]_i$. Thus, calcium signaling in type II cell PL secretion is unlikely to be related to increased $[Ca^{2+}]_i$.

$[Ca^{+2}]_l$ is the Critical Determinant for Surfactant Secretion

Calcium in ER stores is in equilibrium between free and protein-bound states. If the free calcium in stores is chelated or released, the equilibrium shifts, decreasing the amount of bound calcium. BAPTA in its esterified form will easily access ER stores (Miyata, et al, *Am. J. Physiol.* 261: H1123–H1134, 1991; Blatter and Wier, *Biophys. J.,* 58: 1491–1499, 1990) where it is de-esterified. The high affinity of BAPTA for calcium (160 nM) competes effectively with the calcium-binding proteins there, and decreases bound calcium. Thus, calcium signaling activates surfactant secretion by altering $[Ca^{2+}]_I$, not by increasing $[Ca^{2+}]_i$.

ER calcium ($[Ca2+]_1$) was measured directly, applying a combination of fura2ff and $Mn^{2+}$ to quench cytosolic fura2ff fluorescence. This approach has been used previously as a means to measure $[Ca^{2+}]_i$. (Renard-Rooney, et al, *J. Biol. Chem.* 268: 23601–23610, 1993; Dorn, et al, *Br .J Pharmacol.,* 97: 163–170, 1989; Kuroki, et al, *Biochem. J.* 115: 115–119, 1991; Miyata, et al, *Am. J. Physiol.* 261: H1123–H1134, 1991). This analysis highlighted the fact that BAPTA and calcium-releasing secretagogues all decreased $[Ca^{2+}]_i$. PMA, which does not release calcium from stores, had no effect on $[Ca^{2+}]_i$. These findings are best explained by postulating that surfactant secretion, as elicited by calcium-active secretagogues, is triggered by a decrease in the free calcium ($[Ca^{2+}]_I$) and/or bound calcium in the ER. Alternatively, the process of calcium release, rather then the consequent decrease in $[Ca^{2+}]_I$, causes secretion.

ER calcium stores regulate, directly or indirectly, lamellar body movement to the cell surface for extrusion. For example, $Ca^{2+}$ release may alter the conformation of a $Ca^{2+}$-binding protein that spans the ER membrane, such as IP3R. (Mikoshiba, K, *Curr. Opin. Neurobiol,* 7: 339–345. 1997). In changing configuration, IP3R may initiate a signal to move lamellar bodies to the cell surface.

The observations using SP-A both support the importance of $[Ca^{2+}]_I$ in signaling surfactant secretion and suggest a means by which SP-A inhibits secretagogue-induced surfactant secretion. SP-A binds a type II cell membrane receptor (SPAR), inhibiting surfactant secretion. (Strayer, et al, *Exp. Cell Res.* 226: 90–97, 1996; Rice, et al, *J. Appl. Physiol.* 63: 692–698, 1987; Kuroki, et al, *Biochem. J.* 263: 17596–17602, 1988; Kuroki, et al, *Proc. Natl. Acad. Sci. USA* 85: 5566–5570, 1988). It also modulates the secretagogue-induced $Ca^{2+}$ transients. (Sano, et al, *Am. J. Physiol.* 253: C679–C686, 1987; Strayer, et al, *Rec. Signal Transd.* 7: 111–120, 1997; Pian, et al, *Biochim. Biophys. Acta* 960: 43–53, 1988; Dorn, et al, *Br. J. Pharmacol,* 97: 163–170, 1989). It is noteworthy that Io- and TG-induced increases in $[Ca^{2+}]_i$ were also partially inhibited by SP-A (and restored if SP-A-SPAR interaction is blocked with anti-SPAR antibody, (Strayer, et al, *Exp. Cell Res.* 226: 90–97, 1996), since Io and TG act on ER stores directly. The ability of SP-A to decrease secretagogue-induced increases in $[Ca^{2+}]_i$ implies that SP-A alters the availability of calcium for release.

The fact that SP-A increased $[Ca^{2+}]_I$ in a high percentage of type II cells, then, both helps substantiate the proposed mechanism for the activity of calcium-releasing secretagogues and implies that the activity of SP-A in inhibiting their action is by increasing $[Ca^{2+}]_I$. The mechanism(s) by which SP-A does this is unclear. SP-A might, for example, increase the avidity with which stored calcium is bound, or, alternatively, increase the activity of the calcium pump across the ER store membrane.

The studies with PMA emphasize the suggested relationship between the ability of a secretagogue to elicit calcium transients and its dependence on calcium for signaling secretion. PMA secretagogue activity circumvents calcium signaling. (Strayer, et al, *Rec. Signal Transd.* 7: 111–120, 1997). PMA also does not alter $[Ca^{2+}]_i$. SP-A inhibition of PMA-induced secretion probably involves mechanisms other than SP-A-induced increases in $[Ca^{2+}]_I$.

Combining calcium-releasing secretagogues does not increase secretion, only PMA augments secretion that is elicited by individual calcium-releasing secretagogues. Combinations including BAPTA+TG and BAPTA+PMA killed the cells. Apoptosis associated with TG has been previously reported. (Bian, et al, *Am. J. Physiol.* 272: C1241–1249, 1997; He, et al, *J. Cell Biol.* 138: 1219–1228, 1997). Still, these data imply that PMA activates secretion either via a different signaling mechanism or, less likely, distal to calcium release in the pathway activated by calcium-releasing secretagogues.

The extent to which the current data apply to other systems of $Ca^{2+}$-related secretion is not clear. In some experimental systems, BAPTA has no clear effect on secretory activity (Rotondo, et al, *Thromb. Haemost.* 78: 919–925, 1997), while in many experimental systems BAPTA chelation of $Ca^{2+}$ inhibits cellular secretion. (Ko, et al, *Br. J. Pharmacol,* 121: 150–156, 1997; Vainio, et al, *J. Cell Physiol.,* 169: 538–543, 1996). In cell types other than type II cells, BAPTA inhibited secretagogue activities of the same compounds whose secretagogue activities it mimicked here. (Suchard, et al, *J. Innumol,* 152: 290–300, 1994; Xu, et al *J. Cell Sci.* 109: 1605–1613, 1996). Several studies describe BAPTA and, for example, Io having parallel effects in cellular secretion. (Xu, et al *J. Cell Sci.* 109: 1605–1613, 1996). However, BAPTA did not activate secretion in any of these systems.

The present invention focuses attention on calcium in stores and away from $[Ca^{2+}]_i$, as a key effector in signaling type II pneumocyte surfactant secretion. The extent to which similar mechanisms may operate in other calcium-dependent cell activation pathways in other cell types is not known. These findings have clinical ramifications. An intracellular chelator of divalent cations, for example BAPTA-AM, is used to treat conditions wherein an increase in surfactant secretion is desired. These conditions include (see also supra), but are not limited to, infection; respiratory distress syndrome; pulmonary injury such as trauma, inhalation or toxic exposure, drowning, external irradiation, administration of a compound that causes pulmonary injury, or a pulmonary complication of a systemic disease.

What is claimed is:

1. A method of treating a respiratory distress syndrome in a mammal, comprising administering a therapeutically effective amount of an agent comprising an intracellular calcium chelator that activates pulmonary surfactant secretion without increasing the cytosolic free calcium concentration ($[Ca^{+2}]i$) in said mammal, wherein said intracellular calcium chelator comprises BAPTA-AM.

2. The method of claim 1, wherein the amount of BAPTA-AM is between 25 and 100 $\mu$M.

3. The method of claim 1, wherein said agent is administered by an aerosol, nebulization or liquid instillation.

4. A method of inhibiting a respiratory distress syndrome in a mammal, comprising administering a therapeutically effective amount of an agent comprising an intracellular calcium chelator that activates pulmonary surfactant secretion without increasing the cytosolic free calcium concentration ($[Ca^{+2}]i$) in said mammal, wherein said intracellular calcium chelator comprises BAPTA-AM.

5. The method of claim 4, wherein the amount of BAPTA-AM is between 25 and 100 $\mu$M.

6. The method of claim 4, wherein said agent is administered by an aerosol, nebulization or liquid instillation.

* * * * *